(12) United States Patent
Nguyen et al.

(10) Patent No.: US 11,905,518 B2
(45) Date of Patent: Feb. 20, 2024

(54) SMALL AUXIN UPREGULATED (SAUR) GENE FOR THE IMPROVEMENT OF ROOT SYSTEM ARCHITECTURE, WATERLOGGING TOLERANCE, DROUGHT RESISTANCE AND YIELD IN PLANTS AND METHODS OF USES

(71) Applicant: Curators of the University of Missouri, Columbia, MO (US)

(72) Inventors: Henry T. Nguyen, Columbia, MO (US); Heng Ye, Columbia, MO (US); Babu Valliyodan, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/969,229

(22) PCT Filed: Feb. 12, 2019

(86) PCT No.: PCT/US2019/017703
§ 371 (c)(1),
(2) Date: Aug. 12, 2020

(87) PCT Pub. No.: WO2019/157522
PCT Pub. Date: Aug. 15, 2019

(65) Prior Publication Data
US 2021/0002661 A1    Jan. 7, 2021

Related U.S. Application Data

(60) Provisional application No. 62/629,264, filed on Feb. 12, 2018.

(51) Int. Cl.
*C12N 15/82* (2006.01)
*C12Q 1/6895* (2018.01)

(52) U.S. Cl.
CPC ..... *C12N 15/8273* (2013.01); *C12N 15/8262* (2013.01); *C12N 15/8294* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,485,066 A | 11/1984 | Balthis et al. |
| 4,873,182 A | 10/1989 | Delprato et al. |
| 4,945,050 A | 7/1990 | Sanford et al. |
| 5,023,179 A | 6/1991 | Lam et al. |
| 5,096,825 A | 3/1992 | Barr et al. |
| 5,110,732 A | 5/1992 | Benfey et al. |
| 5,269,463 A | 12/1993 | Jefferson |
| 5,364,780 A | 11/1994 | Hershey et al. |
| 5,380,831 A | 1/1995 | Adang et al. |
| 5,399,680 A | 3/1995 | Zhu et al. |
| 5,401,836 A | 3/1995 | Baszcynski et al. |
| 5,436,391 A | 7/1995 | Fujimoto et al. |
| 5,459,252 A | 10/1995 | Conkling et al. |
| 5,466,785 A | 11/1995 | de Framond |
| 5,563,055 A | 10/1996 | Townsend et al. |
| 5,569,597 A | 10/1996 | Grimsley et al. |
| 5,589,367 A | 12/1996 | Donson et al. |
| 5,591,616 A | 1/1997 | Hiei et al. |
| 5,602,321 A | 2/1997 | John |
| 5,604,121 A | 2/1997 | Hilder et al. |
| 5,605,793 A | 2/1997 | Stemmer |
| 5,608,142 A | 3/1997 | Barton et al. |
| 5,608,144 A | 3/1997 | Baden et al. |
| 5,608,149 A | 3/1997 | Barry et al. |
| 5,625,136 A | 4/1997 | Koziel et al. |
| 5,633,363 A | 5/1997 | Colbert et al. |
| 5,641,876 A | 6/1997 | McElroy et al. |
| 5,670,356 A | 9/1997 | Sherf et al. |
| 5,703,409 A | 12/1997 | Fukumitsu et al. |
| 5,750,386 A | 5/1998 | Conkling et al. |
| 5,789,156 A | 8/1998 | Bujard et al. |
| 5,814,618 A | 9/1998 | Bujard et al. |
| 5,837,458 A | 11/1998 | Minshull et al. |
| 5,837,876 A | 11/1998 | Conkling et al. |
| 5,866,785 A | 2/1999 | Donson et al. |
| 5,874,304 A | 2/1999 | Zolotukhin et al. |

(Continued)

FOREIGN PATENT DOCUMENTS

| | | |
|---|---|---|
| EP | 0138341 A2 | 4/1985 |
| EP | 0295959 A3 | 12/1988 |

(Continued)

OTHER PUBLICATIONS

Stortenbeker and Bemer. "The SAUR gene family: the plant's toolbox for adaptation of growth and development". Journal of Experimental Botany. 70 (1):17-27. (Year: 2019).*
Armstrong et al. "Mechanisms of flood tolerance in plants". Acta Botanica Neerlandica. 43(4): 307-358. (Year: 1994).*
Labow et al., Conversion of the Iac Repressor into an Allosterically Regulated Transcriptional Activator for Mammalian Cells; Molecular and Cellular Biology; 1990, pp. 3343-3356.
Lam, 8 Analysis of Tissue-Specific Elements in the CaMV 35S Promoter; 18-pages.
Lamppa, The Chlorophyll a/b-binding Protein Inserts into the Thylakoids Independent of Its Cognate Transit Peptide; The Journal of Biological Chemistry; 1988, vol. 263, No. 29, pp. 14996-14999.
Langridge et al., Dual promoter of Agrobacterium tumefaciens mannopine synthase genes is regulated by plant growth hormones; Proc. Natl. Acad. Sci., 1989, vol. 86, pp. 3219-3223.
Langridge et al., A Zein Gene of Maize Is Transcribed from Two Widely Separated Promoter Regions; Cell, 1983, vol. 34, pp. 1015-1022.

(Continued)

*Primary Examiner* — Matthew R Keogh
*Assistant Examiner* — David R Byrnes
(74) *Attorney, Agent, or Firm* — Stinson LLP

(57) ABSTRACT

Disclosed are modified plants and methods for producing modified plants having a modified 5'-untranslated region of small auxin upregulated protein flooding tolerance (SAUR_FT) gene. Modified plants disclosed herein have at least one of an increased root system architecture, an increased waterlogging tolerance, an increased drought tolerance, and combinations thereof.

12 Claims, 18 Drawing Sheets

(56) References Cited

U.S. PATENT DOCUMENTS

| | | | |
|---|---|---|---|
| 5,879,918 | A | 3/1999 | Tomes et al. |
| 5,885,801 | A | 3/1999 | Rao |
| 5,885,802 | A | 3/1999 | Rao |
| 5,886,244 | A | 3/1999 | Tomes et al. |
| 5,889,190 | A | 3/1999 | Donson et al. |
| 5,889,191 | A | 3/1999 | Turpen |
| 5,932,782 | A | 8/1999 | Bidney |
| 5,981,840 | A | 11/1999 | Zhao et al. |
| 5,986,171 | A | 11/1999 | Barbour et al. |
| 5,990,389 | A | 11/1999 | Rao et al. |
| 5,992,931 | A | 11/1999 | LaPointe et al. |
| 6,072,050 | A | 6/2000 | Bowen et al. |
| 6,177,611 | B1 | 1/2001 | Rice |
| 6,225,529 | B1 | 5/2001 | Lappegard et al. |
| 6,232,529 | B1 | 5/2001 | Singletary et al. |
| 6,338,168 | B1 | 1/2002 | Valentine |
| 6,521,427 | B1 | 2/2003 | Evans |
| 6,818,395 | B1 | 11/2004 | Quake et al. |
| 6,858,778 | B1 | 2/2005 | Jung et al. |
| 6,921,815 | B2 | 7/2005 | Niu et al. |
| 7,009,087 | B1 | 3/2006 | Sewalt et al. |
| 7,101,057 | B2 | 9/2006 | Parker et al. |
| 7,102,057 | B2 | 9/2006 | Lanahan et al. |
| 7,521,178 | B1 | 4/2009 | Asada et al. |
| 2004/0082770 | A1 | 4/2004 | Castle et al. |
| 2009/0062521 | A1 | 3/2009 | Fujihara |
| 2012/0180165 | A1* | 7/2012 | Hatzfeld ............ C12N 15/8261 536/23.6 |

FOREIGN PATENT DOCUMENTS

| | | |
|---|---|---|
| EP | 0292435 B1 | 7/1995 |
| EP | 0332581 B1 | 12/1996 |
| EP | 1721908 A1 | 11/2006 |
| WO | 199321335 | 10/1993 |
| WO | 199400977 | 1/1994 |
| WO | 199706268 | 2/1997 |
| WO | 199800533 | 2/1998 |
| WO | 199820122 | 5/1998 |
| WO | 199925821 | 5/1999 |
| WO | 199925840 | 5/1999 |
| WO | 199925853 | 5/1999 |
| WO | 199925854 | 5/1999 |
| WO | 199925855 | 5/1999 |
| WO | 199943838 | 9/1999 |
| WO | 199961619 | 12/1999 |
| WO | 200011177 A1 | 3/2000 |
| WO | 200012733 A1 | 3/2000 |
| WO | 200017364 A2 | 3/2000 |
| WO | 2002036782 A3 | 5/2002 |
| WO | 2003006651 A2 | 1/2003 |
| WO | 2004022771 A2 | 3/2004 |
| WO | 2005082923 A1 | 9/2005 |

OTHER PUBLICATIONS

Lawrence et al., Alterations in the Chlamydomonas Plastocyanin Transit in Vivo Protein Accumulation; The Journal of Biological Chemistry; 1997, vol. 272, No. 33, pp. 20357-20363.

Lawton et al., Expression of a soybean , Beta-conclycinin gene under the control of the Cauliflower Mosaic Virus 35S and 19S promoters in transformed petunia tissues; Plant Molecular Biology; 1987, vol. 9, pp. 315-324.

Leach et al., Promoter analysis of the highly expressed roIC and roID root-inducing genes of Agrobacterium rhizogenes: enhancer and tissue-specific DNA determinants are dissociated; Plant Science; 1991, vol. 79, pp. 69-76.

Li et al., Physiological roles of long noncoding RNAs: insight from knockout mice; CellPress; 9-pages.

Lindstrom et al., Expression of Soybean Lectin Gene Deletions in Tobacco; Developmental Genetics; 1990, vol. 11, pp. 160-167.

Lommel et al., Identification of the Maize Chlorotic Mottle Virus Capsid Protein Cistron and Characterization of its Subgenomic Messenger RNA; Virology, 1991; vol. 181, pp. 382-385.

Lonneborg et al., Construction of Subtractive cDNA Library Using Magnetic Beads and PCR; 2011, 10-pages.

Ludwig et al., A regulatory Gene as a Novel Visiible Marker for Maize Transformation; 1990, 3-pages.

Macdjak et al., Internal initiation of translation medicated by teh 5' leader of a cellular mRNA; Letters to Nature, 1991, vol. 353, 5-pages.

Martinez et al., Structure, Evolution and Anaerobic Regulation of a Nuclear Gene Encoding Cytosolic Glyceraldehyde-3-phosphate Dehydrogenase from Maize; J. Mol. Biol.; 1989, vol. 208, pp. 551-565.

Masumura et al., cDNA cloning of an mRNA encoding a sulfur-rich 10 kDa prolamin polypeptide in rice seeds; Plant Molecular Biology, 1989, vol. 12, pp. 123-130.

Matsuoka et al., Tissue-specific light-regulated expression directed by the promoter of a C4 gene, maize pyruvate, orthophosphate dikinase, in a C3 plant, rice; Proc. Natl. Acad. Sci, 1993, vol. 90, pp. 9586-9590.

McCabe et al., Stable Transformation of Soybean (*Glycine Max*) By Particle Acceleration; Nature Publishing Group, 1988, 5-pages.

McCormick et al., Leaf disc transformation of cultivated tomato (*L. esculentum*) using Agrobacterium tumefaciens; Plant Cell Reports, 1986, vol. 8, pp. 81-84.

McNellis et al., Glucocorticoid-inducible expression of a bacterial avirulence gene in transgenic *Arabidopsis* induces hypersensitive cell death; The Plant Journal, 1998, vol. 14, No. 2, pp. 247-257.

Miao et al., Ammonia-Regulated Expression of a Soybean Gene Encoding Cytosolic Glutamine Synthetase in Transgenic Lotus corniculatus; The Plant Cell, 1991, vol. 3, pp. 11-22.

Mickey et al., The Inducible lac Operator-Repressor System Is Functional in Mammalian Cells; Cell, 1987, vol. 48, pp. 555-566.

Mogen et al., Upstream Sequences Other than AAUAAA Are Required for Efficient Messenger RNA 3'-End Formation in Plants; The Plant Cell, 1990, vol. 2, pp. 1261-1272.

Moore et al., Strategies for the in vitro Evolution of Protein Function: Enzyme Evolution by Random Recombination of Improved Sequences; J. Mol. Biol., 1997, vol. 272, pp. 336-347.

Munroe et al., Tales of poly(A): a review; (Protein synthesis; poly(A)-binding protein; 3'-translational enhancer); Gene, 1990, vol. 91, pp. 151-158.

Murashige et al., A Revised Medium for Rapid Growth and Bio Assays with Tobacco Tissue Cultures; Physiologia Plantarum, 1962, vol. 15, 26-pages.

Murray et al., Codon usage in plant genes; Nucleic Acids Research; 1989, vol. 17, No. 2, 22-pages.

Myers et al., Optimal alignments in linear space; CABIOS; 1988, vol. 4, No. 1, pp. 11-17.

Needleman et al., A General Method Applicable to the Search for Similarities in the Amino Acid Sequence of Two Proteins; J. Mol. Biol., 1970, vol. 48, pp. 443-453.

Nguyen et al., Mapping of Quantitative Trait Loci Associated with Resistance to Phytophthora sojae and Flooding Tolerance in Soybean; 2012, 13-pages.

Nguyen et al., Breeding for Drought Resistance in Rice: Physiology and Molecular Genetics Considerations; Crop Sci., 1997, vol. 37, pp. 1426-1434.

Nomura et al., Embryogenesis From Microinjected Single Cells In A Carrot Cell Suspension Culture; Plant Science, 1986, vol. 44, pp. 53-58.

Odell et al., Identification of DNA sequences required for activity of the cauliflower mosaic virus 35S promoter; Nature, 1985, vol. 313, 3-pages.

Oliva et al., Evidence that Tetracycline Analogs Whose Primary Target Is Not the Bacterial Ribosome Cause Lysis of *Escherichia coli*; Antimicrobial Agenets And Chemotherapy, 1992; vol. 36, No. 5, pp. 913-919.

Orozco et al., Localization of light-inducible and tissue-specific regions of the spinach ribulose bisphosphate carboxylase/oxygenase (rubisco) activase promoter in transgenic tobacco plants; Plant Molecular Biology, 1993, vol. 23, pp. 1129-1138.

Paszkowski et al., Direct gene transfer to plants; The EMBO Journal, 1984, vol. 3, No. 12, pp. 2717-2722.

(56) References Cited

OTHER PUBLICATIONS

Pearson et al., Improved tools for biological sequence comparison; Proc. Natl. Acad. Sci, 1988, vol. 85, pp. 2444-2448.
Pease et al., Light-generated oligonucleotide arrays for rapid DNA sequence analysis; Proc. Natl. Acad. Sci., 1994, vol. 91, pp. 5022-5026.
Peattie et al., Direct chemical method for sequencing RNA; Proc. Natl. Acad. Sci, 1979, vol. 76, pp. 1760-1764.
Pedersen et al., Sequence Analysis and Characterization of a Maize Gene Encoding a High-sulfur Zein Protein of Mr 15, 000; The Journal of Biological Chemistry; 1986, vol. 261, No. 14, pp. 6279-6284.
Porta et al., Use of Viral Replicons for the Expression of Genes in Plants; Molecular Biotechnology, 1996, vol. 5, 13-pages.
Potrykus et al., Molecular and general genetics of a hybrid foreign gene introduced into tobacco by direct gene transfer; Mol. Gen Genet, 1985, vol. 199, pp. 169-177.
Poulsen et al., Characterization of an rbcS gene from Nicotiana plumbaginifolia and expression of an rbcS-CAT chimeric gene in homologous and heterologous nuclear background; Mol Gen Genet; 1986, vol. 205, pp. 193-200.
Proudfoot, Poly(A) Singnals; Cell, 1991, vol. 64, pp. 671-674.
Ralston et al., Sequence of Three bronze Alleles of Maize and Correlation With the Genetic Fine Structure; Genetics Society of America, 13-pages.
Reese et al., Tetrahedron Report No. 56; Tetrahedron, 1978, vol. 34, pp. 3143-3179.
Reich et al., Efficient Transformation of Alfalfa Protoplatsts By the Intranuclear Microinjection of Ti Plasmids; ; 1986, Nature Publ. Group, 4-pages.
Reines et al., Elongation factor SII-dependent transcription by RNA polymerase II through a sequence-specific DNA-binding protein; Proc. Natl. Acad. Sci, Biochemistry, 1993, vol. 90, pp. 1917-1921.
Reznikoff, MicroReview; The lactose operon-controlling elements: a complex paradigm; Molecular Microbiology, 1992, vol. 6, No. 17, pp. 2419-2422.
Riggs et al., Stable transformation of tobacco by electroporation: Evidence for plasmid concatenation; Proc. Natl. Acad. Sci., Genetics, 1986, vol. 83, pp. 5602-5606.
Yamamoto et al., The Promoter of a Pine Photosynthetic Gene Allows Expression of a beta-Glucuronidasee Reporter Gene in Transgenic Rice Plants in a Light-Independent but Tissue-Specific Manner; Plant Cell Physiol., 1994, vol. 35, No. 5, pp. 773-778.
Yamamoto et al., Root-specific genes from tobacco and Arabidopsis homologous to an evolutionarily conserved gene family of membrane channel proteins; Nucleic Acids Research, 1009, vol. 18, No. 24, 1-page.
Yamamoto et al., Light-responsive elements of the tobacco PSI-D gene are located both upstream and within the transcribed region; The Plant Journal, 1997, vol. 12, No. 2, pp. 255-265.
Yang et al., Maize sucrose synthase-1 promoter directs phloem cell-specific expression of Gus gene in transgenic tobacco plants; Proc. Natl. Acad. Sci., 1990, vol. 87, pp. 4144-4148.
Yao et al., Drosophila ultraspiracle Modulates Ecdysone Recptor Function via Heterodimer Formation; Cell, 1992, vol. 71, 10-pages.
Yarranton, Inducible vectors for expression in mammalian cell; Current Opinion in Biotechnology, 1992, vol. 3, pp. 506-511.
Ye et al., Correction for Ye et al., Nrf2- and ATF4-Dependent Upregulation of xCT Modulates the Sensitivity of T24 Bladder Carcinoma Cells to Proteasome Inhibition; 1-page.
Zambetti et al., A mutant p53 protein is required for maintenance of the transformed phenotype in cells transformed with p53 plus ras cDNAs; Proc. Natl. Acad. Sci., 1992, vol. 89, pp. 3952-3956.
Zhang et al., Transgenic rice plants produced by electroporation-mediated plasmid uptake into protoplasts; Plant Cell Reports, 1988, vol. 7, pp. 379-384.
Zhang et al., Directed evolution of a fucosidase from a galactosidase by DNA shuffling and screening; Proc. Natl. Acad. Sci., 1997, vol. 94, pp. 4504-4509.
Zhao et al., Immunological Characterization and Chloroplast Localizatioin of the Tryptophan Biosynthetic Enzymes of the Flowering Plant *Arabidopsis thaliana*; The Journal of Biological Chemistry, 1995, vol. 270, No. 11, 7-pages.
Ausubel et al., Short Protocols in Molecular Biology, Third Edition; 1995, 1-page.
Narang et al., Improved Phosphotriester Method for teh Synthesis of Gene Fragments; Methods in Enzymology, 1979, vol. 68, 9-pages.
Akond et al., SNP-Based Genetic Linkage Map of Soybean Using the SoySNP6K Illumina Infinium BeadChip Genotyping Array; Southern Illinois University Carbondale, 2013; Department of Plant, Soil, and Agricultural Systems 12-pages.
Akond et al., Effect of Two Row Spaces on Several Agronomic Traits in Soybean [*Glycine max* (L.) Merr.]; Atlas Journal of Plant Biology; 2013, vol. 1, No. 2, pp. 18-23.
Allison et al., The Nucleotide Sequence of the Coding Region of Tobacco Etch Virus Genomic RNA: Evidence for the Synthesis of a Single Polyprotein; Virology, 1986, vol. 154, pp. 9-20.
Aoyama et al., A glucocorticoid-mediated transcriptional induction system in transgenic plants; The Plant Journal; 1997, vol. 11, No. 3, pp. 608-612.
Archer et al., Current Views on Chlorplast Protein Import and Hypotheses on the Origin of the Transport Mechanism; Journal of Bioenergetics and Biomembranes; 1090, vol. 22, No. 6, 24-pages.
Arai-Sanoh et al., Deep rooting conferred by Deeper Rooting 1 enhances rice yield in paddy fields; Scientific Reports, 2014, vol. 4, 6-pages.
Baim et al., A chimeric mammalian transactivator based. on the lac repressor that is regulated by temperature and isopropyl (8-D-thiogalactopyranoside; Proc. Natl. Acad. Sci., 1991, Biochemistry, vol. 88, pp. 5072-5076.
Ballas et al., Efficient functioning of plant promoters and poly(A) sites in Xenopus oocytes; Nucleic Acids Research; 1989, vol. 17, No. 19, 13-pages.
Bansal et al., Transient expression from cab-ml and rbcS-m3 promoter sequences is different in mesophyll and bundle sheath cells in maize leaves; Proc. Natl. Acad. Sci., 1992, vol. 89, pp. 3654-3658.
Beaucage et al., Deoxynucleoside phosphoramidites—a new class of key intermediates for deoxypolynucleotide synthesis; T1981, etrahedron Lett. vol. 22, pp. 1859-1862.
Belanger et al., Molecular Basis for Allelic Polymorphism of the Maize Globulin-1 Gene; Genetics Society of America; 1991, 10-pages.
Bogusz et al., Nonlegume Expression Hemoglobin Genes Retain Organ-Specific in Heterologous Transgenic Plants; The Plant Cell, 1990, vol. 2, pp. 633-641.
Bolte et al., The N-myristoylated Rab-GTPase m-Rabmc is involved in post-Golgi trafficking events to the lytic vacuole in plant cells; Journal of Cell Science, 2003, vol. 117, pp. 943-954.
Brown et al., lac Repressor Can Regulate Expression from a Hybrid SV40 Early Promotor Containing a lac Operator in Animal Cells; Cell, 1987, vol. 49, pp. 603-612.
Brown et al., Chemicals Synthesis and Cloning of a Tyrosine tRNA Gene; 43-pages.
Bruce et al., The paradox of plastid transit peptides: conservation of function despite divergence in primary structure; Biochimica et Biophysica Acta, 2001, vol. 1541, pp. 2-21.
Bucksch et al., IPlant Physiology, 2012, vol. 166, pp. 470-486. mage-Based High-Throughput Field Phenotyping of Crop Roots 1[W][Open]; Breakthrough Technologies.
Campbell et al., Codon Usage in Higher Plants, Green Algae, and Cyanobacteria; Plant Physiol., 1990, vol. 92, pp. 1-11.
Canevascini et al., Tissue-Specific Expression and Promoter Analysis of the Tobacco ltp1 Gene; Plant Physiol., 1996, vol. 112, pp. 513-524.
Cashmore, Nuclear Genes Encoding The Small Subunit Of Ribulose-1,5-Bisphosphate Carboxylase; 10-pages.
Chalfie et al., Green Fluorescent Protein as a Marker for Gene Expression; Science; 1994, vol. 263, 5-pages.
Chandler et al., Two Regulatory Genes of the Maize Anthocyanin Pathway Are Homologous: Isolation of B Utilizing R Genomic Sequences; The Plant Cell, 1989, vol. 1, pp. 1175-1183.

(56) References Cited

OTHER PUBLICATIONS

Christopherson et al., Ecdysteroid-dependent regulation of genes in mammalian cells by a *Drosophila ecdysone* receptor and chimeric transactivators; Proc. Natl., Acad. Sci, 1992, vol. 89, pp. 6314-6318.
Clark et al., Mutations at the Transit Peptide-Mature Protein Junction Separate Two Cleavage Events during Chloroplast Import of the Chlorophyll a/b-binding Protein *; The Journal of Biological Chemistry; 1989, vol. 264, No. 29, pp. 17544-17550.
Copeland et al., Recombineering: A Powerful New Tool for Mouse Functional Genomics; Nature Reviews: Genetics; 2001, vol. 2, 11-pages.
Cordero et al., Expression of a maize proteinase inhibitor gene is induced in response to wounding and fungal infection: systemic wound-response of a monocot gene; The Plant Journal, 1994, vol. 6, No. 2, pp. 141-150.
Cornelious et al., Identification of QTLs underlying water-logging tolerance in soybean; Molecular Breeding, 2005, vol. 16, pp. 103-112.
Cornelious et al., Yield Potential and Waterlogging Tolerance of Selected Near-Isogenic Lines and Recombinant Inbred Lines from Two Southern Soybean Populations; Journal of Crop Improvement; 17-pages.
Crameri et al., Molecular evolution of an arsenate detoxification pathway by DNA shuffling; Nature Biology, 1997, vol. 15, 3-pages.
Crameri et al., Improved Green Fluorescent Protein by Molecular Evolution Using DNA Shuffling; Nature Biotechnology; 1996, vol. 147, 5-pages.
Crameri et al., DNA shuffling of a family of genes from diverse species accelerates directed evolution; Nature, 1998, vol. 39, 4-pages.
Crossway et al., Micromanipulatin Techniques in Plant Biotechnology; BioTechniques, 1986, vol. 4, 16-pages.
Crossway et al., Integration of foreign DNA following microinjection of tobacco mesophyll protoplasts; Mol Gen Genet, 1986, vol. 202, pp. 179-185.
Czako et al., Differential manifestation of see mortality induces by seed-specific expression of the gene for diphtheria toxin A chain in *Arabidopsis* and tobacco; Mol. Gen Genet, 1992, vol. 235, pp. 33-40.
Daniell, New tools for chloroplast genetic engineering; Nature Biotechnology, 1999, vol. 17, 2-pages.
Das et al., Digital imaging of root traits (DIRT): a high-throughput computing and collaboration platform for field-based root phenomics; Plant Methods, 2015, vol. 11, No. 51, 12-pages.
Datta et al., Genetically Engineered Fertile Indica-Rice Recovered From Protoplasts; Nature; 1990, 5-pages.
Degenkolb et al., Structural Requirements of Tetracycline-Tet Repressor Interaction: Determination of Equilibrium Binding Constants for Tetracycline Analogs with the Tet Repressor; Antimicrobial Agents and Chemotherapy, 1991, vol. 35, No. 8, pp. 1591-1595.
Della-Cioppa et al., Protein Trafficking in Plant Cell; Plant Physiol., 2987, vol. 84, pp. 965-968.
Dennis et al., Molecular analysis of the alcohol dehydrogenase (Adh1) gene of maize; Nucleic Acids Research; 1984, vol. 12, No. 9, 18-pages.
Deuschle et al., RNA Polymerase II Transcription Blocked by *Escherichia coli* Lac Repressor; Science, vol. 248, 5-pages.
Deuschle et al., Regulated expression of foreign genes in mammalian cells under the control of coliphage T3 Rna polymerase and lac repressor; Proc. Nati. Acad. Sci., 1989, vol. 86, pp. 5400-5404.
Ebert et al., Identification of an essential upstream element in the nopaline synthase promoter by stable and transient assays; Proc. Natl. Acad. Aci; 1987, vol. 84, pp. 5745-5749.
Elroy-Stein et al., Cap-independent translation of mRNA conferred by encephalomyocarditis virus 5' sequence improves the performance of the vaccinia virus/bacteriophage T7 hybrid expression system; Proc. Natl. Acad. Sci, 1989, vol. 86, pp. 6126-6130.
Emanuelsson et al., Prediction of organellar targeting signals; Biochimica et Biophysica Acta, 2001, pp. 114-119.

Emanuelsson et al., Predicting Subcellular Localization of Proteins Based on their N-terminal Amino Acid Sequence; J. Mol. Biol., 2000, vol. 300, pp. 1005-1016.
Fetter et al., Interactions between Plasma Membrane Aquaporins Modulate Their Water Channel Activity; The Plant Cell, 2004, vol. 16, pp. 215-228.
Figge et al., Stringent Regulation of Stably Integrated Chloramphenicol Acetyl Transferase Genes by *E. coli* lac Repressor in Monkey Cells; Cell, 1988, vol. 52, pp. 713-722.
Filho et al., Mitochondrial and chloroplast targeting sequences in tandem modify protein import specificity in plant organelles; Plant Molecular Biology, 1996, vol. 30, pp. 769-780.
Fodor et al., Light-directed, spatially addressable parallel chemical synthesis; Science, 1991, vol. 251, pp. 767.
Franken et al., The duplicated chalcone synthase genes C2 and Whp (white pollen) of *Zea mays* are independently regulated; evidence for translational control of Whp expression by the anthocyanin intensifying gene in; The EMBO Journal, 1991, vol. 10, No. 9 pp. 2605-2612.
Fromm et al., Inheritance and Expression of Chimeric Genes in the Progeny of Transgenic Maize Plants; Bio/ Technology, 1990, vol. 8, 9-pages.
Fuerst et al., Transfer of the inducible lac repressor/operator system from *Escherichia coli* to a vaccinia virus expression vector; Proc. Nati. Acad. Sci., Biochemestry; 1989, vol. 86, pp. 2549-2553.
Gallie, Translational control of cellular and viral mRNAs; Plant Molecular Biology; 1996, vol. 32, pp. 145-158.
Gallie et al., Eukaryotic Viral 5'-Leader Sequences Act As Translational Enhancers In Eukaryotes And Prokaryotes; Molecular Biology of RNA, 1989, pp. 237-256.
Gallie et al., The tobacco etch viral 5' leader and poly(A) tail are funtionally synergistic regulators of translation; Gene, 1995, vol. 165, pp. 233-238.
Gan et al., Inhibition of Leaf Senescence by Autoregulated Production of Cytokinin; Science; 1995, vol. 270, 4-pages.
Gatz et al., Regulation of a modified CaMV 35S promoter by the Tn10-encoded Tet repressor in transgenic tobacco; Mol Gen Genet (1991), vol. 227, pp. 229-237.
Gatz, Chemical Control of Gene Expression; Annu. Rev. Plant Physiol. Plant Mol. Biol., 1997, vol. 48, pp. 89-108.
Gill et al., Negative effect of the transcriptional activator GAL4; Nature, 1988, vol. 334, 4-pages.
Goodman, Fermentation and Mutational Development of the Tetracyclines; 2020, 3-pages.
Gordon-Kamm et al., Transformation of Maize Cells and Regeneration of Fertile Transgenic Plants; The Plant Cell, 1990, vol. 2, pp. 603-618.
Gossen et al., Tight control of gene expression in mammalian cells by tetracycline-responsive promoters; Proc. Nati. Acad. Sci., Cell Biology, vol. 89, pp. 5547-5551.
Gotor et al., Analysis of three tissue-specific elements form the wheat Cab-1 enhancer; The Plant Journal, 1993, vol. 3, No. 4, pp. 509-518.
Graham et al., Wound-induced Proteinase Inhibitors from Tomato Leaves; The Journal of Biological Chemistry, 1984-1985, vol. 260, No. 11, pp. 6555-6560. Part 1.
Graham et al., Wound-induced Proteinase Inhibitors from Tomato Leaves; The Journal of Biological Chemistry, 1984-1985, vol. 260, No. 11, pp. 6561-6564. Part 2.
Graham et al., Expression patterns of vascular-specific promoters RolC and Sh in transgenic potatoes and their use in engineering PLRV-resistant plants; Plant Molecular Biology; 1997, vol. 33, pp. 729-735.
Graham et al., Accumulation of a Metallo-Carboxypeptidase Inhibitor in Leaves of Wounded Potato Plants; Biochemical and Biophysical Research Communications; 1981, vol. 101, No. 4, pp. 1164-1170.
Grant et al., SoyBase, the USDA-ARS soybean genetics and genomics database; Nucleic Acids Research, 2010, vol. 38, Database issue D843-D846.

(56) References Cited

OTHER PUBLICATIONS

Guerineau et al., Effect of deletions in the cauliflower mosaic virus polyadenylation sequence on the choice of the bolyadenylation sites in tobacco protoplasts; Mol. Gen. Genet, 1991, vol. 226, pp. 141-144.

Guevara-Garcia et al., Tissue-specific and wound-inducible pattern of expression of the mannopine synthase promoter is determined by the interaction between positive and negative cis-regulatory elements.

Hadlington et al., Sorting of soluble proteins in the secretory pathway of plants; Cell Biology, 8-pages.

Hansen et al., Wound-inducible and organ-speci@c expression of ORF13 from Agrobacterium rhizogenes 8196 T-NA in transgenic tobacco plants; Mol Gen Genet (1997), vol. 254, pp. 337-343.

Heijne et al., CHLPEP—A Database of Chloroplast Transit Peptides; Plant Molecular Biology Reporter, 1991, vol. 9, No. 2, pp. 104-126.

Hepler et al., Nuclear concentration and mitotic dispersion of the essential cell cycle protein, p13SUcl, examined in living cells; Proc. Natd. Acad. Sci. Cell Biology, 1994, vol. 91, pp. 2176-2180.

Hirel et al., Forcing expression of a soybean root glutamine synthetase gene in tobacco leaves induces a native gene encoding cytosolic enzyme; Plant Molecular Biology; 1992, vol. 20, pp. 207-218.

Hudspeth et al., Structure and expression of the maize gene encoding the phospoenopyruvate carboxylase isozyme involved in C4 photosynthesis; Plant Molecular Biology, 1989, vol. 12, pp. 579-589.

Hund et al., A consensus map of QTLs controlling the root length of maize; Plant Soil (2011), vol. 344, pp. 143-158.

Hush et al., Quantification of microtubule dynamics in living plant cells using fluorescence redistribution after photobleaching; Journal of Cell Science, 1994, vol. 107, pp. 775-784.

Jefferson, Assaying Chimeric Genes in Plants: The GUS Gene Fusion System; Plant Molecular Biology Reporter: 1987, vol. 5, No. 4, pp. 387-405.

Jitsuyama, Morphological root responses of soybean to rhizosphere hypoxia reflect waterlogging tolerance; Can. J. Plant Sci. (2015), vol. 95, pp. 999-1005.

Jobling et al., Enhanced translation of chimaeric messenger RNAs containing a plant viral untranslated leader sequence; Nature, 1987, vol. 325, No. 12, 4-pages.

Joshi, Putative polyadenylation signals in nuclear genes of highter plants: a compilation and analysis; Nucleic Acids Research; 1987, vol. 15, No. 23, 14-pages.

Karlin et al., Methods for assessing the statistical significance of molecular sequence features by using general scoring schemes; Proc. Natl. Acad. Sci, Evolution; 1990, vol. 87, pp. 2264-2268.

Kawamata et al., Temporal and Spatial Pattern of Expression of the Pea Phenylalanine Ammonia-Lyase Genel Promoter in Transgenic Tobacco; Plant Cell Physiol., 1997, vol. 38, No. 7, pp. 792-803.

Keller et al., specific expression of a novel cell wall hydroxyproline-rich glycoprotein gene in lateral root initiation; Genes & Development, 1989, vol. 3, pp. 1639-1646.

Keller et al., Vascular-Specific Expression of the Bean GRP 1.8 Gene 1s Negatively Regulated; The Plant Cell, 1991, vol. 3, pp. 1051-1061.

Kim et al., Comparative analysis of endogenous hormones level in two soybean( *Glycine max* L.) lines differing in waterlogging tolerance; Frontiers in Plant Science; 2015, 13-pages.

Kirihara et al., Isolation and sequence of a gene encoding a methionine-rich 10-kDa zein protein from maize; Gene, 1988, vol. 71, pp. 359-370.

Klein et al., High-velocity microprojectiles for delivering nucleic acids into living cells; Nature, 1987, vol. 327, 4-pages.

Kleinschmidt et al., Dynamic of Repressor-Operator Recognition: The Tn10-Encoded Tetracycline Resistance Control; Biochemistry, 1988, vol. 27, pp. 1094-1104.

Kohler et al., The maize GapC4 promoter confers anaerobic reporter gene expression and shows homology to the maize anthocyanin regulatory locus C1; Plant Molecular Biology, 1995, vol. 29, pp. 1293-1298.

Koziel et al., Field Performance of Elite Transgenic Maise Plants Expressing an Insecticidal Protein Derived from Bacillus thuringiensis; Nature Publishing Group; 1993, 7-pages.

Kozlowski et al., Atelosteogenesis; Fortschr. Rontgenstr, 1984, vol. 140, No. 2, pp. 224-225.

Kramer et al., Causes of Injury to Flooded Tobacco Plants; Department of Botany, Duke University; 5-pages.

Kridl et al., Isolation and characterization of an expressed napin gene from *Brassica rapa*; Seed Science Research, 1991, vol. 1, pp. 209-219.

Kriz et al.,, Structural and transcriptional analysis of DNA sequences flanking genes that encode 19 kilodalton zeins; Mol. Gen. Genet; 1987, vol. 207, pp. 90-98.

Kunkel, Rapid and efficient site-specific mutagenesis witho ut phenotypic selection; Prox. Natl. Acad. Sci, 1985, vol. 82, pp. 488-492.

Kunkel et al., Rapid and Efficient Site-Specific Mutagenesis without Phenotypic Selection; Methods in Enzymology, 1987, vol. 154, 16-pages.

Kwon et al., Identification of a Light-Responsive Region of the Nuclear Gene Encoding the B Subunit of Chloroplast Glyceraldehyde 3-Phosphate Dehydrogenase from *Arabidopsis thaliana*; Plant Physiol, 1994, vol. 105, pp. 357-367.

Rinehart et al., Tissue-Specific and Developmental Regulation of Cotton Gene FbL2A1; Demonstration of Promoter Activity in Trangenic Plants; Fiber Technology Division; 11-pages.

Rochester et al., The structure and expression of maize genes encoding the major heat shock protein, hsp70; The EMBO Journal; 1986, vol. 5, No. 3, pp. 451-458.

Romer et al., Expression of the Genes Encoding The Early Carotenoid Biosynthetic Enzymes In Capsicum Annuum; Biochemical and Biophysical Research Communications; 1993, vol. 196, No. 3, 10-pages.

Russell et al., Tissue-specific expression in transgenic maize of four endosperm promoters from maize and rice; Transgenic Research; 1997, vol. 6, pp. 157-168.

Sadok et al., Crops Yield Increase Under Water-Limited Conditions: Review of Recent Physiological Advances for Soybean Genetic Improvement; 25-pages.

Sakazono et al., Variation in Root Development Response to Flooding among 92 Soybean Lines during Early Growth Stages; Plant Production Science; 10-pages.

Safacon et al., A dissection of the cauliflower mosaic virus polyadenylation signal; Genes & Development; 1990, vol. 5, pp. 141-149.

Sanger et al., Characteristics of a strong promoter from figwort mosaic virus: comparison with the analogous 35S promoter from cauliflower mosaic virus and the regulated mannopine synthase promoter; Plant Molecular Biology, 1990, vol. 14, pp. 433-443.

Schena et al., A steroid-inducible gene expression system for plant cells; Proc. Natl. Acad. Sci, 1991, vol. 88, pp. 10421-10425.

Schmutz et al., Genome sequence of the palaeopolyploid soybean; Nature; 2010, vol. 463, No. 14, 6-pages.

Schnell et al., Signal Peptide Analogs Derived fromTw o Chloroplast Precursors Interact with the Signal Recognition Systemof the Chloroplast Envelope *; The Journal of Biological Chemistry; 1991, vol. 266, No. 5, pp. 3335-3342.

Schubert et al., Cloning of the Alcaligenes eutrophus Genes for Synthesis of Poly-3-Hydroxybutyric Acid (PHB) and Synthesis of PHB in *Escherichia coli*; Journal of Bacteriology, 1988, vol. 170, No. 12, pp. 5837-5847.

Schwob et al., Molecular analysis of three maize 22 kDa auxin-binding protein genes—transient promoter expression and regulatory regions; The Plant Journal, 1993, vol. 4, No. 3, pp. 423-432.

Shah et al., Engineering Herbicide Tolerance in Transgenic Plants; Science, vol. 233, 5-pages.

Shimamoto et al., Fertile transgenic rice plants regenerated from transformed protoplasts; Letters to Nature, 3-pages.

Ausubel et al., Short Protocols in Molecular Biology, Third Edition; Biochemical Education, 1996, vol. 24, No. 1, 1-page.

Shimamoto et al., Fertile transgenic rice plants regenerated from transformed protoplasts; Letters To Nature; 1989, vol. 338, 3-pages.

(56) References Cited

OTHER PUBLICATIONS

Silva-Filho, One ticket for multiple destinations: dual targeting of proteins to distinct subcellular location; Current Opinion in Plant Biology, 2003, vol. 6, pp. 589-595.
Simpson et al., Photosynthesis-Associated Gene Families: Differences in Response to Tissue-Specific and Environmental Factors; Science, vol. 233, 6-pages.
Singh-Gasson et al., Maskless fabrication of light-directed oligonucleotide microarrays using a digital micromirror array; Nature America Inc., 1996, 5-pages.
Smith et al., Rapid appearance of an mRNA correlated with ethylene synthesis encoding a protein of molecular weight 35000; Planta; 1986, vol. 168, pp. 94-100.
Smith et al., Comparison of Biosequences; Advances in Applied Mathematics 2, 1981, vol. 2, pp. 482-489.
Song et al., Genetic Characterization of the Soybean Nested Association Mapping Population; Plant Geneome; 28-pages.
Stemmer, Rapid evolution of a protein in vitro by DNA shuffling; Letters to Nature; 1994, vol. 370, 3-pages.
Stemmer, DNA shuffling by random fragmentation and reassembly: in vitro recomination for molecular evolution; Proc. Natl. Acad. Sci, 1994, vol. 91, pp. 10747-10751.
Sullivan et al., Isolation and characterization of a maize chlorophyll a/b binding protein gene that produces high levels of mRNA in the dark; Mol. Gen. Genet, 1989, vol. 215, pp. 431-440.
Sullivan et al., Crop Ecology, Production & Managment; Evaluatin On-Farm Flooding Impacts on Soybean; Crop Sci., 2001, vol. 41, pp. 93-100.
Teeri et al., Gene fusions to lacZ reveal new expression patterns of chimeric genes in transgenic plants; The EMBO Journal; 1989, vol. 8, No. 2, pp. 343-350.
Thompson et al., Structural Elements Regulating Zein Gene Expression; BioEssays, 1989, vol. 10, No. 4, 8-pages.
Tomes et al., 16 Direct DNA Transfer into Intact Plant Cells Via Microprojectile Bombardment; Plant Cell, Tissue and Organ Culture; 1995, 17-pages.
Trachsel et al., Shovelomics: high throughput phenotyping of maize (*Zea mays* L.) root architecture in the field; Plant Soil, 2011, vol. 341, pp. 75-87.
Uga et al., Control of root system architecture by Deeper Rooting 1 increases rice yield under drought conditions; Nature Genetics; 2013, vol. 45, No. 9, 9-pages.
Valliyodan et al., Expression of Root-Related Transcription Factors Associated with Flooding Tolerance of Soybean (*Glycine max*); Int. J. Mol. Sci., 2014, vol. 15, pp. 17622-17643.
Van Damme et al., Molecular cloning of mannose-binding lectins from Clivia miniata; Plant Molecular Biology, 1994, vol. 24, pp. 825-830.
Van Camp et al., Tissue-Specific Activity of Two Manganese Superoxide Dismutase Promoters in Transgenic Tobacco; Plant Physiol, 1996, vol. 112, pp. 525-535.
Van Tunen et al., Cloing of the two chalcone flavanone isomerase genes from Petunia hybrida: coordinate, light-regulated and differential expression of flavonoid genes; The EMBO Journal, 1988, vol. 7, No. 5, pp. 1257-1263.
Vasil et al., Rapid Production of Transgenic Wheat Plants by Direct Bombardment of Cultured Immature Embryos; Nature, 1983, 6-pages.
Vasil et al., Herbicide Resistant Fertile Tunsgenic Wheat Plants Obtained By Microprojectile Bombardment Of Regeneuble Embryogenic Calws; Nature, 1992, 8-pages.
Vodkin et al., Structure and Expression of Soybean Lectin Genes; Chemical Taxonomy, Molecular Biology, and Function of Plant Lectins, 1983, pp. 87-98.
Vogel et al., Analysis of chromosome replication by a BrdU antibody technique; Chromosoma (Berl), 1989, vol. 98, pp. 335-341.
Wada et al., Codon usage tabulated from teh GenBank genetic sequence data; Nucleic Acids Research, 1990, Supplement vol. 18, 45-pages.
Walker et al., DNA sequences required for anaerobic expression of the maize alcohol dehydrogenase 1 gene; Proc. Natl. Acad. Sci., Biochemistry; 1987, vol. 84, pp. 6624-6628.
Wandelt et al., Sequence of a 21 kd zein gene from maize containing an in-frame stop codon; Nucleic Acids Research, 1989, vol. 17, No. 6, 1-page.
Wang et al., Characterization of cis-Acting Elements Regulating Transcription from the Promoter of a Constitutively Active Rice Actin Gene; Molecular and Cellular Biology, 1992, pp. 3399-3406.
Wasson et al., Traits and selection strategies to improve root systems and water uptake in water-limited wheat crops; Journal of Experimental Botany, 2012, vol. 63, No. 9, pp. 3485-3498.
Weeks et al., Rapid Productio of Multiple Independent Lines of Fertile Transgenic Wheat (*Triticum aestivum*); Plant Physiol, 1993, vol. 102, pp. 1077-1084.
Wen et al., High-Level Secretion of Functional Green Fluorescent Protein From Transgenic Tobacco Cell Cultures: Characterization and Sensing; 2003, 10-pages.
Wenzler et al., Sucrose-regulated expression of a chimeric potato tuber gene in leaves of transgenic tobacco plants; Plant Molecular Biology, 1989, vol. 13, pp. 347-354.
Williamson et al., Nucleotide sequence of barley chymotrypsin inhibitor-2 (CI-2) and its expression in normal and high-lysine barley; Eur. J. Biochem., 1987, vol. 165, pp. 99-106.
Wyborski et al., Analysis of inducers of the E.coli lac repressor system in mammalian cells and whole animals; Nucleic Acids Research, 1991, vol. 19, No. 17, pp. 4647-4653.

\* cited by examiner

SMALL AUXIN UPREGULATED (SAUR) GENE FOR THE IMPROVEMENT OF ROOT SYSTEM ARCHITECTURE, WATERLOGGING TOLERANCE, DROUGHT RESISTANCE AND YIELD IN PLANTS AND METHODS OF USES

CROSS REFERENCE TO RELATED APPLICATIONS

This application is a U.S. National Phase Application of PCT/US2019/017703 (published as WO 2019/157522), filed on Feb. 12, 2019, which claims priority to U.S. Provisional Patent Application Ser. No. 62/629,264, filed on Feb. 12, 2018, the disclosures of which are hereby incorporated by reference in its their entireties.

BACKGROUND OF THE DISCLOSURE

The present disclosure relates generally to the development of crop plants having improved root system architecture, waterlogging tolerance, drought resistance and yield. More particularly, the present disclosure is directed to modified plants having improved root system architecture, waterlogging tolerance, drought resistance and yield. The present disclosure is also directed to methods for selecting plants having improved root system architecture, waterlogging tolerance, drought resistance and yield. The present disclosure is further directed to methods for producing crop plants having improved root system architecture, waterlogging tolerance, drought resistance and yield.

Waterlogging injury limits the growth and productivity of crop plants, especially on poorly drained soils. Root system architecture is an important developmental and agronomic trait, and plays vital roles in plant adaptation and productivity under normal, excessive and limited-water environments. A deeper and more proliferative root system helps plants extract enough water and nutrients under these environmental conditions. The mechanisms of waterlogging tolerance and root system architecture are still not clear.

Accordingly, there exists a continuing need to develop crop plants identify the underlying mechanisms for waterlogging tolerance and regulation of root system architecture. These traits can lead to the development of crop plants having increased yield, tolerance to drought and waterlogging, better root system architecture, and better agronomic quality.

BRIEF DESCRIPTION OF THE DISCLOSURE

The present disclosure relates generally to the development of crop plants having improved root system architecture, waterlogging tolerance, drought resistance and yield. More particularly, the present disclosure is directed to modified plants having improved root system architecture, waterlogging tolerance, drought resistance and yield. The present disclosure is also directed to methods for selecting plants having improved root system architecture, waterlogging tolerance, drought resistance and yield. The present disclosure is further directed to methods for producing crop plants having improved root system architecture, waterlogging tolerance, drought resistance and yield.

In one aspect, the present disclosure is directed to a modified plant comprising at least one of a modified 5'-untranslated region of small auxin upregulated protein flooding tolerance (SAUR_FT) gene, a modified 5'-untranslated region of SAUR_FT gene homolog, and a SAUR_FT gene ortholog. In one embodiment, the modified plant is a transgenic plant. In one embodiment, the modified plant is produced by gene editing.

In one aspect, the present disclosure is directed to a method of selecting a plant having at least one of increased root system architecture, increased waterlogging tolerance, increased drought tolerance, increased yield, and combinations thereof, the method comprising obtaining a sample of the plant and analyzing small auxin upregulated protein flooding tolerance (SAUR_FT) gene.

In one aspect, the present disclosure is directed to a method of producing a modified plant comprising at least one of an increased root system architecture, an increased waterlogging tolerance, an increased drought tolerance, and combinations thereof, the method comprising: reducing expression of small auxin upregulated protein flooding tolerance (SAUR_FT) gene.

In one aspect, the present disclosure is directed to a modified plant having increased waterlogging tolerance comprising over-expression of GmARF20.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A. Field phenotyping for flooding tolerance using FIS. FIS were used to represent waterlogging tolerance levels, which were rated from 1 to 5; 1=no apparent injury, 5=most plants severely injured or dead. FIG. 1B. Phenotypic distributions of FIS across three years. The FIS were collected for 3 years as indicated. "M" stands for mean of the FIS of the population; while "S" stands for standard deviation of the FIS of the population. The arrows pointed the average performances in flooding injury scores of the two parents. S99-2281 is an elite and sensitive parent; while PI 561271 is an exotic and tolerant parent. Broad sense heritability ($H^2$) was calculated for FIS across three years using model: $y_{ijk} = \mu + g_i + t_j + (gt)_{ij} + b_k(j) + e_{ijk}$.

FIG. 6A. Genotypic differences between the sensitive and tolerant alleles of SAUR-FT in transgenic hairy roots in medium plates. Two independent transgenic roots of each of the 3 types were grown on one plate. Data shown are mean±SE of 15 plates. Duncan-multiple-comparison was performed to categorize the data into "a" and "b" or "c" and "d" at p-value of <0.0001. FIG. 6B. Effect of over-expressed SAUR-FT on root growth in medium plates. Two to four independent transgenic roots of each of the 2 types were grown on one plate. Data shown are mean±SE of 16 plates. T-test was performed to compare the means between over-expression of cDNA and control. The genetic background used in this experiment is the tolerant parent PI 561271. FIG. 6C. Effect of over-expressed SAUR-FT on root growth in soil. Twenty independent transgenic composite transgenic plants of each of the 2 types were constructed and grown in the soil pots. T-test was performed to compare the means between over-expression of cDNA and control. FIG. 6D. Effect of over-expressed SAUR-FT on waterlogging tolerance in soil. Twelve independent transgenic composite transgenic plants of each of the 2 types were constructed and grown in the soil pots. The plants were subjected to waterlogging stress for 10 days and allowed for recovery for 7 days. The genetic background used in this experiment is the tolerant parent PI 561271

FIG. 7C Expression of GmARF20 in the roots during waterlogging treatment. GmARF20 in soybean is the closest homologue of AtARF19 in *Arabidopsis* (Ha et al. 2013). Data shown are means±standard deviations of two biological replicates and each replicate contains 10 plants.

FIG. 8A Images of the NILs in the field at the reproductive stage, R5. Yields (FIG. 8B) and 100 seeds weights (FIG. 8C) of the NILs in the field. Data shown are means±standard deviations of yield estimated from 2.44 m rows with three replications. Eighty seeds were planted for each row with a 0.76 m row spacing. The percentages on the columns indicate the portion that increased in "AA" compared with "aa". (FIG. 8D) Representative images of roots of NILs at R5 growth stage from the field. (FIG. 8E) Genotypic difference in root area at the R5 stage among the NILs. The two sets of NILs were planted in the field under none-stress conditions. The images of the roots were analyzed using Digital Imaging of Root Traits. Data shown are means±standard deviations of 10 plants for each line. (FIG. 8F) Yield of the NILs in greenhouse. Data shown are means±standard deviations of yield estimated for single plant based on 22 plants for each line. Student's-t-test was performed to compare means of traits between NILs with the sensitive allele "aa" and the tolerant allele "AA".

FIG. 12A Images of the NILs in the greenhouse after 14 days of transplanting. FIG. 12B Images of the roots of NILs in the greenhouse after 14 days of transplanting. Plants were transplanted into bigger soil pots at V1 growth stage. All plants have similar amount roots left during transplanting.

DETAILED DESCRIPTION

Figure 1A:
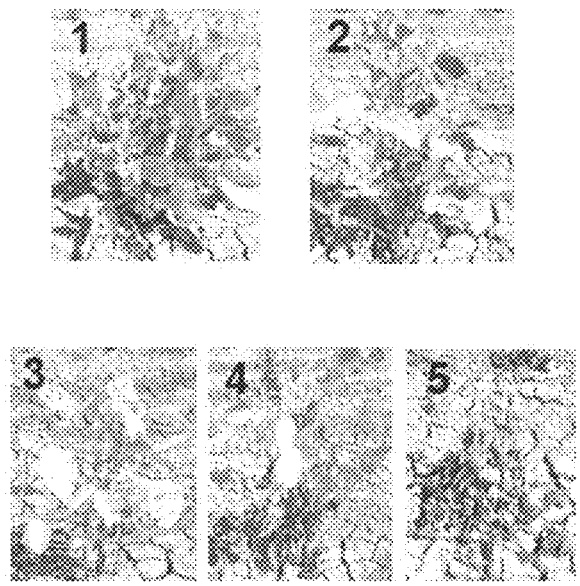
FIGS. 1A and 1B depict phenotyping for flooding tolerance and phenotypic distributions of flooding injury scores (FIS) of the RIL mapping population.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

While the present disclosure is susceptible to various modifications and alternative forms, exemplary embodiments thereof are shown by way of example in the drawings and are herein described in detail. It should be understood, however, that the description of exemplary embodiments is not intended to limit the disclosure to the particular forms disclosed, but on the contrary, the intention is to cover all modifications, equivalents and alternatives falling within the scope of the disclosure as defined by the embodiments above and the claims below. Reference should therefore be made to the embodiments above and claims below for interpreting the scope of the present disclosure.

Unless defined otherwise, all technical and scientific terms used herein have the same meaning as commonly understood by one of skill in the art to which the invention pertains. Although any methods and materials similar to or equivalent to those described herein can be used in the practice or testing of the present disclosure, the preferred methods and materials are described herein. Moreover, reference to an element by the indefinite article "a" or "an" does not exclude the possibility that more than one element is present, unless the context clearly requires that there be one and only one element. The indefinite article "a" or "an" thus usually includes "at least one."

Disclosed herein are modified plants and methods of producing modified plants using the genomic regions (4 kilo base pairs including promoter, 5'-untranslated region, coding region, 3'-untralted region) underlying the SAUR_FT gene (Glyma.03g029600) on chromosome 3 in soybean. The plants and methods described herein result in improved root system architecture, waterlogging tolerance, drought resistance, and yield.

As used herein, a "nucleic acid" sequence means a DNA or RNA sequence. The term encompasses sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As used herein, "recombinant," when used in connection with a nucleic acid molecule, means a molecule that has been created or modified through deliberate human intervention such as by genetic engineering. For example, a recombinant nucleic acid molecule is one having a nucleotide sequence that has been modified to include an artificial nucleotide sequence or to include some other nucleotide sequence that is not present within its native (non-recombinant) form.

Further, a recombinant nucleic acid molecule has a structure that is not identical to that of any naturally occurring nucleic acid molecule or to that of any fragment of a naturally occurring genomic nucleic acid molecule spanning more than one gene. A recombinant nucleic acid molecule also includes, without limitation, (a) a nucleic acid molecule having a sequence of a naturally occurring genomic or extrachromosomal nucleic acid molecule, but which is not flanked by the coding sequences that flank the sequence in its natural position; (b) a nucleic acid molecule incorporated into a construct, expression cassette or vector, or into a host cell's genome such that the resulting polynucleotide is not identical to any naturally occurring vector or genomic DNA; (c) a separate nucleic acid molecule such as a cDNA, a genomic fragment, a fragment produced by polymerase chain reaction (PCR) or a restriction fragment; and (d) a recombinant nucleic acid molecule having a nucleotide sequence that is part of a hybrid gene (i.e., a gene encoding a fusion protein). As such, a recombinant nucleic acid molecule can be modified (chemically or enzymatically) or unmodified DNA or RNA, whether fully or partially single-stranded or double-stranded or even triple-stranded.

Methods for synthesizing nucleic acid molecules are well known in the art, such as cloning and digestion of the appropriate sequences, as well as direct chemical synthesis (e.g., ink-jet deposition and electrochemical synthesis). Methods of cloning nucleic acid molecules are described, for example, in Ausubel et al. (1995), supra; Copeland et al. (2001) *Nat. Rev. Genet.* 2:769-779; *PCR Cloning Protocols*, 2nd ed. (Chen & Janes eds., Humana Press 2002); and Sambrook & Russell (2001), supra. Methods of direct chemical synthesis of nucleic acid molecules include, but are not limited to, the phosphotriester methods of Reese (1978) *Tetrahedron* 34:3143-3179 and Narang et al. (1979) *Methods Enzymol.* 68:90-98; the phosphodiester method of Brown et al. (1979) *Methods Enzymol.* 68:109-151; the diethylphosphoramidate method of Beaucage et al. (1981) *Tetrahedron Lett.* 22:1859-1862; and the solid support methods of Fodor et al. (1991) *Science* 251:767-773; Pease et al. (1994) *Proc. Natl. Acad. Sci. USA* 91:5022-5026; and Singh-Gasson et al. (1999) *Nature Biotechnol.* 17:974-978; as well as U.S. Pat. No. 4,485,066. See also, Peattie (1979) *Proc. Natl. Acad. Sci. USA* 76:1760-1764; as well as EP Patent No. 1 721 908; Int'l Patent Application Publication Nos. WO 2004/022770 and WO 2005/082923; US Patent Application Publication No. 2009/0062521; and U.S. Pat. Nos. 6,521,427; 6,818,395 and 7,521,178.

For nucleotide sequences, "variant" refers to a substantially similar nucleotide sequence to a nucleotide sequence of a recombinant nucleic acid molecule as described herein, for example, a substantially similar nucleotide sequence encoding a SAUR_FT protein. For nucleotide sequences, a variant comprises a nucleotide sequence having deletions (i.e., truncations) at the 5' and/or 3' end, deletions and/or additions of one or more nucleotides at one or more internal sites compared to the nucleotide sequence of the recombinant nucleic acid molecules as described herein; and/or substitution of one or more nucleotides at one or more sites compared to the nucleotide sequence of the recombinant nucleic acid molecules described herein. One of skill in the art understands that variants are constructed in a manner to maintain the open reading frame.

Conservative variants include those nucleotide sequences that, because of the degeneracy of the genetic code, result in a functionally active modified SAUR_FT protein as described herein. Naturally occurring allelic variants can be identified by using well-known molecular biology techniques such as, for example, polymerase chain reaction (PCR) and hybridization techniques. Variant nucleotide sequences also can include synthetically derived sequences, such as those generated, for example, by site-directed mutagenesis but which still provide a functionally active modified SAUR_FT protein. Generally, variants of a nucleotide sequence of the recombinant nucleic acid molecules as described herein will have at least about 70%, 75%, 80%, 85%, 90%, 91%, 92%, 93%, 94%, 95%, 96%, 97%, 98%, 99% or more sequence identity to the nucleotide sequence of the recombinant nucleic acid molecules as determined by sequence alignment programs and parameters as described elsewhere herein.

Methods of mutating and altering nucleotide sequences, as well as DNA shuffling, are well known in the art. See, Crameri et al. (1997) *Nature Biotech.* 15:436-438; Crameri et al. (1998) *Nature* 391:288-291; Kunkel (1985) *Proc. Natl. Acad. Sci. USA* 82:488-492; Kunkel et al. (1987) *Methods in Enzymol.* 154:367-382; Moore et al. (1997) *J. Mol. Biol.* 272:336-347; Stemmer (1994) *Proc. Natl. Acad. Sci. USA* 91:10747-10751; Stemmer (1994) *Nature* 370:389-391; Zhang et al. (1997) *Proc. Natl. Acad. Sci. USA* 94:4504-4509; and *Techniques in Molecular Biology* (Walker & Gaastra eds., MacMillan Publishing Co. 1983) and the references cited therein; as well as U.S. Pat. Nos. 4,873,192; 5,605,793 and 5,837,458. As such, the nucleic acid molecules as described herein can have many modifications.

Variants of the recombinant nucleic acid molecules described herein also can be evaluated by comparing the percent sequence identity between the polypeptide encoded by a variant and the polypeptide encoded by a reference nucleic acid molecule. Thus, for example, an isolated nucleic acid molecule can be one that encodes a polypeptide with a given percent sequence identity to the polypeptide of interest. Percent sequence identity between any two polypeptides can be calculated using sequence alignment programs and parameters described elsewhere herein. Where any given pair of polynucleotides of the present disclosure is evaluated by comparison of the percent sequence identity shared by the two polypeptides they encode, the percent sequence identity between the two encoded polypeptides can be at least about 70%, 75%, 80%, 85%, 90%, 91%, 92%, 93%, 94%, 95%, 96%, 97%, 98%, 99% or more sequence identity.

Determining percent sequence identity between any two sequences can be accomplished using a mathematical algorithm. Non-limiting examples of such mathematical algorithms include, but are not limited to, the algorithm of Myers & Miller (1988) *CABIOS* 4:11-17; the local alignment algorithm of Smith et al. (1981) *Adv. Appl. Math.* 2:482-489; the global alignment algorithm of Needleman & Wunsch (1970) *J. Mol. Biol.* 48:443-453; the search-for-local-alignment method of Pearson & Lipman (1988) *Proc. Natl. Acad. Sci. USA* 85:2444-2448; the algorithm of Karlin & Altschul (1990) *Proc. Natl. Acad. Sci. USA* 87:2264-2268, modified as in Karlin & Altschul (1993) *Proc. Natl. Acad. Sci. USA* 90:5873-5877.

The present disclosure therefore includes recombinant nucleic acid molecules having a nucleotide sequence that encodes a modified substrate protein of a pathogen-specific protease, where the modified substrate protein has a heterologous protease recognition sequence and can be incorporated into nucleic acid constructs such as expression cassettes and vectors.

Compositions of the present disclosure also include nucleic acid constructs, such as expression cassettes or vectors, having plant promoters operably linked with a nucleic acid molecule that encodes SAUR_FT proteins for use in transforming plant cells, plant parts and plants. In addition, the constructs can include a nucleic acid molecule that encodes SAUR_FT proteins, particularly when such SAUR_FT proteins are not native/not endogenous to the plant cell, plant part or plant to be transformed.

As used herein, "nucleic acid construct" refers to an oligonucleotide or polynucleotide composed of deoxyribonucleotides, ribonucleotides or combinations thereof having incorporated therein the nucleotide sequences described herein. The nucleotide construct can be used for transforming organisms such as plants. In this manner, plant promoters operably linked to nucleotide sequences for SAUR_FT proteins and modified SAUR_FT proteins as described herein are provided in nucleic acid constructs for expression in a plant cell, plant part or plant.

As used herein, "expression cassette" refers to a nucleic acid molecule having at least a control sequence operably linked to a coding sequence.

As used herein, "operably linked" means that the elements of the expression cassette are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. Thus, for example, intervening untranslated, yet transcribed, sequences can be present between a promoter and a coding sequence, and the promoter sequence still can be considered "operably linked" to the coding sequence.

As used herein, a "coding sequence" or "coding sequences" refers to a sequence that encodes a particular polypeptide, and is a nucleotide sequence that is transcribed (in the case of DNA) and translated (in the case of mRNA) into a polypeptide in vitro or in vivo when placed under the control of appropriate regulatory sequences. The boundaries of the coding sequence are determined by a start codon at a 5' (amino) terminus and a translation stop codon at a 3' (carboxy) terminus. A coding sequence can include viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence. Examples of coding sequences for use herein include nucleotide sequence that encodes a SAUR_FT protein, a modified SAUR_FT protein or both.

As used herein, "control sequence" or "control sequences" refers to promoters, polyadenylation signals, transcription and translation termination sequences, upstream regulatory domains, origins of replication, internal ribosome entry sites ("IRES"), enhancers, and the like, which collectively provide for replication, transcription and translation of a coding sequence in a recipient host cell. Not all of these control sequences need always be present so long as the selected coding sequence is capable of being replicated, transcribed and translated in an appropriate host cell.

As used herein, a "promoter" refers to a nucleotide region comprising a nucleic acid (i.e., DNA) regulatory sequence, wherein the regulatory sequence is derived from a gene or synthetically created that is capable of binding RNA polymerase and initiating transcription of a downstream (3'-direction) coding sequence. A number of promoters can be used in the expression cassette, including the native promoter of the modified SAUR_FT protein.

Alternatively, promoters can be selected based upon a desired outcome. Such promoters include "constitutive promoters" (where expression of a polynucleotide sequence operably linked to the promoter is unregulated and therefore continuous), "inducible promoters" (where expression of a polynucleotide sequence operably linked to the promoter is induced by an analyte, cofactor, regulatory protein, etc.), and "repressible promoters" (where expression of a polynucleotide sequence operably linked to the promoter is repressed by an analyte, cofactor, regulatory protein, etc.).

As used herein, "plant promoter" refers to a promoter that drives expression in a plant such as a constitutive, inducible (e.g., chemical-, environmental-, pathogen- or wound-inducible), repressible, tissue-preferred or other promoter for use in plants.

Examples of constitutive promoters include, but are not limited to, the rice actin 1 promoter (Wang et al. (1992) *Mol. Cell. Biol.* 12:3399-3406; and U.S. Pat. No. 5,641,876), the CaMV 19S promoter (Lawton et al. (1987) *Plant Mol. Biol.* 9:315-324), the CaMV 35S promoter (Odell et al. (1985) *Nature* 313:810-812), the nos promoter (Ebert et al. (1987) *Proc. Natl. Acad. Sci. USA* 84:5754-5749), the Adh promoter (Walker et al. (1987) *Proc. Natl. Acad. Sci. USA* 84:6624-6628), the sucrose synthase promoter (Yang & Russell (1990) *Proc. Natl. Acad. Sci. USA* 87:4144-4148), the ubiquitin promoters, and the like. See also, U.S. Pat. Nos. 5,608,149; 5,608,144; 5,604,121; 5,569,597; 5,466,785; 5,399,680; 5,268,463; 5,608,142 and 6,177,611.

Examples of chemical-inducible promoters include the maize Tn2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-inducible promoters of interest include steroid-responsive promoters (e.g., the glucocorticoid-inducible promoters in Aoyama & Chua (1997) *Plant J.* 11:605-612; McNellis et al. (1998) *Plant J.* 14:247-257; and Schena et al. (1991) *Proc. Natl. Acad. Sci. USA* 88:10421-10425); tetracycline-inducible and tetracycline-repressible promoters (Gatz et al. (1991) *Mol. Gen. Genet.* 227:229-237; as well as U.S. Pat. Nos. 5,814,618 and 5,789,156); ABA- and turgor-inducible promoters, the auxin-binding protein gene promoter (Schwob et al. (1993) *Plant J.* 4:423-432), the UDP glucose flavonoid glycosyl-transferase gene promoter (Ralston et al. (1988) *Genetics* 119:185-187), the MPI proteinase inhibitor promoter (Cordero et al. (1994) *Plant J.* 6:141-150), and the glyceraldehyde-3-phosphate dehydrogenase gene promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Chemical-inducible promoters therefore can be used to modulate the expression of a nucleotide sequence of interest in a plant by applying an exogenous chemical regulator. Depending upon the objective, the promoter can be a chemical-inducible promoter, whereby application of the chemical induces gene expression, or a chemical-repressible promoter, whereby application of the chemical represses gene expression. See also, Gatz (1997) *Annu. Rev. Plant Physiol. Plant Mol. Biol.* 48:89.

Other inducible promoters include promoters from genes inducibly regulated in response to environmental stress or stimuli such as drought, pathogens, salinity and wounds. See, Graham et al. (1985) *J. Biol. Chem.* 260:6555-6560; Graham et al. (1985) *J. Biol. Chem.* 260:6561-6564; and Smith et al. (1986) *Planta* 168:94-100. Wound-inducible promoters include the metallocarboxypeptidase-inhibitor protein promoter (Graham et al. (1981) *Biochem. Biophys. Res. Comm.* 101:1164-1170).

Examples of tissue-preferred promoters include the rbcS promoter, the ocs, nos and mas promoters that have higher activity in roots or wounded leaf tissue, a truncated (−90 to +8) 35S promoter that directs enhanced expression in roots, an α-tubulin gene promoter that directs expression in roots, as well as promoters derived from zein storage protein genes that direct expression in endosperm. Additional examples of tissue-preferred promoters include the promoters of genes encoding the seed storage proteins (e.g., β-conglycinin, cruciferin, napin and phaseolin), zein or oil body proteins (e.g., oleosin), or promoters of genes involved in fatty acid biosynthesis (e.g., acyl carrier protein, stearoyl-ACP desaturase and fatty acid desaturases (e.g., fad 2-1)), and promoters of other genes expressed during embryo development (e.g., Bce4; Kridl et al. (1991) *Seed Sci. Res.* 1:209-219). Further examples of tissue-specific promoters include the lectin promoter (Lindstrom et al. (1990) *Dev. Genet.* 11:160-167; and Vodkin (1983) *Prog. Clin. Biol. Res.* 138:87-98), the corn alcohol dehydrogenase 1 promoter (Dennis et al. (1984) *Nucleic Acids Res.* 12:3983-4000; and Vogel et al. (1989) *J. Cell. Biochem.* 13: Part D, M350 (Abstract)), corn light harvesting complex (Bansal et al. (1992) *Proc. Natl. Acad. Sci. USA* 89:3654-3658; and Simpson (1986) *Science* 233:34-380), corn heat shock protein (Odell et al. (1985) *Nature* 313:810-812; and Rochester et al. (1986) *EMBO J.* 5:451-458), the pea small subunit RuBP carboxylase promoter (Cashmore, "Nuclear genes encoding the small subunit of ribulose-1,5-bisphosphate carboxylase" 29-38 In: Gen. Eng. of Plants (Plenum Press 1983); and Poulsen et al. (1986) *Mol. Gen. Genet.* 205:193-200), the Ti plasmid mannopine synthase promoter (Langridge et al. (1989) *Proc. Natl. Acad. Sci. USA* 86:3219-3223), the Ti plasmid nopaline synthase promoter (Langridge et al. (1989), supra), the Petunia chalcone isomerase promoter (van Tunen et al. (1988) *EMBO J.* 7:1257-1263), the bean glycine rich protein 1 promoter (Keller et al. (1989) *Genes Dev.* 3:1639-1646), the truncated CaMV 35s promoter (Odell et al. (1985), supra), the potato patatin promoter (Wenzler et al. (1989) *Plant Mol. Biol.* 13:347-354), the root cell promoter (Yamamoto et al. (1990) *Nucleic Acids Res.* 18:7449), the maize zein promoter (Langridge et al. (1983) *Cell* 34:1015-1022; Kriz et al. (1987) *Mol. Gen. Genet.* 207:90-98; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), the globulin-1 gene (Belanger et al. (1991) *Genetics* 129:863-872), the α-tubulin, cab promoter (Sullivan et al. (1989) *Mol. Gen. Genet.* 215:431-440), the PEPCase promoter (Hudspeth & Grula0 (1989) *Plant Mol. Biol.* 12:579-589), the R gene complex-associated promoters (Chandler et al. (1989) *Plant Cell* 1:1175-1183), and the chalcone synthase promoters (Franken et al. (1991) *EMBO J.* 10:2605-2612). See also, Canevascini et al. (1996) *Plant Physiol.* 112:513-524; Guevara-Garcia et al. (1993) *Plant J.* 4:495-505; Hansen et al. (1997) *Mol. Gen. Genet.* 254:337-343; Kawamata et al. (1997) *Plant Cell Physiol.* 38:792-803; Lam (1994) *Results Probl. Cell Differ.* 20:181-196; Matsuoka et al. (1993) *Proc. Natl. Acad. Sci. USA* 90:9586-9590; Orozco et al. (1993) *Plant Mol. Biol.* 23:1129-1138; Rinehart et al. (1996) *Plant Physiol.* 112: 1331-1341; Russell et al. (1997) *Transgenic Res.* 6:157-168; Van Camp et al. (1996) *Plant Physiol.* 112:525-535; Yamamoto et al. (1994) *Plant Cell Physiol.* 35:773-778; and Yamamoto et al. (1997) *Plant J.* 12:255-265.

In some instances, the tissue-preferred promoter can be a leaf-preferred promoter. See, Gan et al. (1995) *Science* 270:1986-1988; Gotor et al. (1993) *Plant J.* 3:509-518; Kwon et al. (1994) *Plant Physiol.* 105:357-367; Matsuoka et al. (1993), supra; Orozco et al. (1993), supra; Yamamoto et al. (1994), supra; and Yamamoto et al. (1997), supra.

In some instances, the tissue-preferred promoter can be a root-preferred promoter. See, Capana et al. (1994) *Plant Mol. Biol.* 25:681-691 (rolB promoter); Hire et al. (1992) *Plant Mol. Biol.* 20:207-218 (soybean root-specific glutamine synthetase gene); Keller & Baumgartner (1991) *Plant Cell* 3:1051-1061 (root-specific control element in the GRP 1.8 gene of French bean); Kuster et al. (1995) *Plant Mol. Biol.* 29:759-772 (VfENOD-GRP3 gene promoter) Miao et al. (1991) *Plant Cell* 3:11-22 (full-length cDNA clone encoding cytosolic glutamine synthetase (GS), which is expressed in roots and root nodules of soybean); and Sanger et al. (1990) *Plant Mol. Biol.* 14:433-443 (root-specific promoter of the mannopine synthase (MAS) gene of *A. tumefaciens*); see also, U.S. Pat. Nos. 5,837,876; 5,750,386; 5,633,363; 5,459,252; 5,401,836; 5,110,732; and 5,023,179. Likewise, Bogusz et al. (1990) *Plant Cell* 2:633-641 describes two root-specific promoters isolated from hemoglobin genes from the nitrogen-fixing nonlegume *Parasponia andersonii* and the related non-nitrogen-fixing nonlegume *Trema tomentosa*. Leach & Aoyagi (1991) *Plant Sci.* 79:69-76 describes an analysis of the promoters of the highly expressed rolC and rolD root-inducing genes of *Agrobacterium rhizogenes*. Teen et al. (1989) *EMBO J.* 8:343-335 describes a gene fusion to lacZ to show that the *Agrobacterium* T-DNA gene encoding octopine synthase is especially active in the epidermis of the root tip and that the TR2' gene is root specific in the intact plant and stimulated by wounding in leaf tissue.

In some instances, the tissue-preferred promoter can be a seed-preferred promoter, which includes both "seed-specific" promoters (i.e., promoters active during seed development such as promoters of seed storage proteins) and "seed-germinating" promoters (i.e., promoters active during seed germination). See, Thompson et al. (1989) *BioEssays* 10:108-113. Examples of seed-preferred promoters include the Cim1 promoter (cytokinin-induced message); the cZ19B1 promoter (maize 19 kDa zein); the myo-inositol-1-phosphate synthase (milps) promoter (Int'l Patent Application Publication No. WO 00/11177; and U.S. Pat. No. 6,225,529); the γ-zein promoter; and the globulin 1 (Glb-1) promoter. For monocots, seed-specific promoters include promoters from maize 15 kDa zein, 22 kDa zein, 27 kDa zein, γ-zein, waxy, shrunken 1, shrunken 2 and Glb-1. See also, Int'l Patent Application Publication No. WO 00/12733, which discloses seed-preferred promoters from end1 and end2 genes. For dicots, seed-specific promoters include promoters from bean β-phaseolin, napin, β-conglycinin, soybean lectin, cruciferin and pea vicilin (Czako et al. (1992) *Mol. Gen. Genet.* 235:33-40). See also, U.S. Pat. No. 5,625,136.

In some instances, the tissue-preferred promoter can be a stalk-preferred promoter. Examples of stalk-preferred promoters include the maize MS8-15 gene promoter (Int'l Patent Application Publication No. WO 98/00533; and U.S. Pat. No. 5,986,174), and the promoters disclosed in Graham et al. (1997) *Plant Mol. Biol.* 33:729-735.

In some instances, the tissue-preferred promoter can be a vascular tissue-preferred promoter. For example, a vascular tissue-preferred promoter can be used to express the SAUR_FT protein in polypexylem and phloem tissue. Examples of vascular tissue-preferred promoters include the *Prunus serotina* prunasin hydrolase gene promoter (Int'l Patent Application Publication No. WO 03/006651), and the promoters disclosed in U.S. Pat. No. 6,921,815.

As an alternative to the promoters listed above, in some instances a low level of expression is desired and can be achieved by using a weak promoter. As used herein, "weak promoter" means a promoter that drives expression of a coding sequence at a low level. As used herein, "low level" means at levels of about 1/1000 transcripts to about 1/100,000 transcripts to about 1/500,000 transcripts. Alternatively, it is recognized that weak promoter also encompasses promoters that are expressed in only a few cells and not in others to give a total low level of expression. Where a promoter is expressed at unacceptably high levels, portions of the promoter sequence can be deleted or modified to decrease expression levels. Weak promoters can be used when designing expression cassettes for SAUR_FT genes. Examples of weak constitutive promoters include the core promoter of the Rsyn7 promoter (Int'l Patent Application Publication No. WO 99/43838 and U.S. Pat. No. 6,072,050), the core 35S CaMV promoter, and the like. Other weak constitutive promoters are described, for example, in U.S. Pat. Nos. 5,608,149; 5,608,144; 5,604,121; 5,569,597; 5,466,785; 5,399,680; 5,268,463; 5,608,142 and 6,177,611.

The expression cassette can include other control sequences 5' to the coding sequence. For example, the expression cassette can include a 5' leader sequence, which can act to enhance translation. Examples of 5' leader sequences can include picornavirus leaders (e.g., encephalomyocarditis virus (EMCV) leader; Elroy-Stein et al. (1989) *Proc. Natl. Acad. Sci. USA* 86:6126-6130); potyvirus leaders (e.g., tobacco etch virus (TEV) leader; Gallie et al. (1995) *Gene* 165:233-238); maize dwarf mosaic virus (MDMV) leader (Allison et al. (1986) *Virology* 154:9-20); human immunoglobulin heavy-chain binding protein (BiP; Macejak et al. (1991) *Nature* 353:90-94); untranslated leader from the coat protein mRNA of alfalfa mosaic virus (AMV RNA 94; Jobling et al. (1987) *Nature* 325:622-625); tobacco mosaic virus (TMV) leader (Gallie et al., "Eukaryotic viral 5'-leader sequences act as translational enhancers in eukaryotes and prokaryotes" 237-256 In: Molecular Biology of RNA (Cech ed., Liss 1989)); and maize chlorotic mottle virus (MCMV) leader (Lommel et al. (1991) *Virology* 81:382-385). See also, Della-Cioppa et al. (1987) *Plant Physiol.* 84:965-968; and Gallie (1996) *Plant Mol. Biol.* 32:145-158. Other methods or sequences known to enhance translation also can be used, for example, introns, and the like.

The expression cassette also can include a coding sequence for the modified SAUR_FT protein. As discussed above, the modified SAUR_FT protein includes a modification of the 5'-UTR of the SAUR_FT gene sequence.

The control sequence(s) and/or the coding sequence can be native/analogous to the host cell or to each other. Alternatively, the control sequence(s) and/or coding sequence can be heterologous to the host cell or to each other. As used herein, "heterologous" refers to a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The expression cassette also can include a transcriptional and/or translational termination region that is functional in plants. The termination region can be native with the transcriptional initiation region (i.e., promoter), can be native with the operably linked coding sequence, can be native with the plant of interest, or can be derived from another source (i.e., foreign or heterologous to the promoter, the coding sequence, the plant host cell, or any combination thereof). Termination regions are typically located downstream (3'-direction) from the coding sequence. Termination regions include the potato proteinase inhibitor (PinII) gene or the Ti-plasmid of *A. tumefaciens*, such as the octopine synthase and nopaline synthase termination regions. See e.g., Ballas et al. (1989) *Nucleic Acids Res.* 17:7891-7903; Guerineau et al. (1991) *Mol. Gen. Genet.* 262:141-144; Joshi et al. (1987) *Nucleic Acid Res.* 15:9627-9639; Mogen et al. (1990) *Plant Cell* 2:1261-1272; Munroe et al. (1990) *Gene* 91:151-158; Proudfoot (1991) *Cell* 64:671-674; and Sanfacon et al. (1991) *Genes Dev.* 5:141-149.

The expression cassette also can include one or more linkers. As used herein, "linker" refers to a nucleotide sequence that functions to link one element of the expression cassette with another without otherwise contributing to the transcription or translation of a nucleotide sequence of interest when present in the expression cassette. The linker can include plasmid sequences, restriction sequences and/or sequences of a 5'-untranslated region (5'-UTR). The length and sequence of the linker can vary and can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000 nucleotides or greater in length.

Just as expression of the SAUR_FT proteins can be targeted to specific tissues or cell types by appropriate use of promoters, it also can be targeted to different locations within a cell of a plant host by appropriate use of signal and/or targeting peptide sequences. Unlike a promoter, which acts at the transcriptional level, signal and/or targeting peptide sequences are part of the initial translation product. Therefore, the expression cassette also can include a signal and/or targeting peptide sequence. Examples of such sequences include the transit peptide for the acyl carrier protein, the small subunit of RUBISCO, plant EPSP synthase, and the like. See, Archer et al. (1990) *J. Bioenerg. Biomemb.* 22:789-810; Clark et al. (1989) *J. Biol. Chem.* 264:17544-17550; Daniell (1999) *Nat. Biotech.* 17:855-856; de Castro Silva Filho et al. (1996) *Plant Mol. Biol.* 30:769-780; Della-Cioppa et al. (1987) *Plant Physiol.* 84:965-968; Lamppa et al. (1988) *J. Biol. Chem.* 263:14996-14999; Lawrence et al. (1997) *J. Biol. Chem.* 272:20357-20363; Romer et al. (1993) *Biochem. Biophys. Res. Commun.* 196:1414-1421; Schmidt et al. (1993) *J. Biol. Chem.* 268:27447-27457; Schnell et al. (1991) *J. Biol. Chem.* 266:3335-3342; Shah et al. (1986) *Science* 233:478-481; Von Heijne et al. (1991) *Plant Mol. Biol. Rep.* 9:104-126; and Zhao et al. (1995) *J. Biol. Chem.* 270:6081-6087; as well as U.S. Pat. No. 6,338,168.

Additional guidance on subcellular targeting of proteins in plants can be found, for example, in Bruce (2001) *Biochim Biophys Acta* 1541:2-21; Emanuelsson et al. (2000) *J. Mol. Biol.* 300:1005-1016; Emanuelsson & von Heijne (2001) *Biochim Biophys Acta* 1541:114-119; Hadlington & Denecke (2000) *Curr. Opin. Plant Biol.* 3:461-468; Nicchitta (2002) *Curr. Opin. Cell Biol.* 14:412-416; and Silva-Filho (2003) *Curr. Opin. Plant Biol.* 6:589-595.

The expression cassette also can include nucleotide sequences encoding agronomic and pesticidal polypeptides, and the like. Such sequences can be stacked with any combination of nucleotide sequences to create plant cells, plants parts and plants with a desired phenotype. For example, the nucleic acid molecule encoding the SAUR_FT proteins can be stacked with nucleotide sequences encoding a pesticidal polypeptide such as a δ-endotoxin. The combinations generated also can include multiple copies of any one of the nucleotide sequences of interest. Examples of other nucleotide sequences of interest include sequences encoding for high oil (U.S. Pat. No. 6,232,529); balanced amino acids (hordothionins; U.S. Pat. Nos. 5,703,409; 5,885,801; 5,885,802 and 5,990,389); barley high lysine (Williamson et al. (1987) *Eur. J. Biochem.* 165:99-106; and Int'l Patent Application Publication No. WO 98/20122); high methionine proteins (Pedersen et al. (1986) *J. Biol. Chem.* 261:6279-6284; Kirihara et al. (1988) *Gene* 71:359-370; and Musumura et al. (1989) *Plant Mol. Biol.* 12:123-130); increased digestibility (modified storage proteins; U.S. Pat. No. 6,858,778); and thioredoxins (U.S. Pat. No. 7,009,087).

The nucleotide sequences encoding the SAUR_FT proteins also can be stacked with nucleotide sequences encoding polypeptides for herbicide resistance (e.g., glyphosate or HPPD resistance; see, e.g., EPSPS genes, GAT genes (Int'l Patent Application Publication Nos. WO 02/36782 and WO 03/092360; and US Patent Application Publication No. 2004/0082770); lectins (Van Damme et al. (1994) *Plant Mol. Biol.* 24:825-830); fumonisin detoxification (U.S. Pat. No. 5,792,931); acetolactate synthase (ALS) mutants that lead to herbicide resistance such as the S4 and/or Hra mutations; inhibitors of glutamine synthase such as phosphinothricin or basta (e.g., bar gene); modified starches (ADPG pyrophosphorylases (AGPase), starch synthases (SS), starch branching enzymes (SBE) and starch debranching enzymes (SDBE)); and polymers or bioplastics (U.S. Pat. No. 5,602,321); beta-ketothiolase, polyhydroxybutyrate synthase and acetoacetyl-CoA reductase (Schubert et al. (1988) *J. Bacteriol.* 170:5837-5847).

The nucleotide sequences encoding the SAUR_FT proteins also can be stacked with nucleotide sequences encoding for agronomic traits such as male sterility (U.S. Pat. No. 5,583,210), stalk strength, flowering time or transformation technology traits such as cell cycle regulation or gene targeting (Int'l Patent Application Publication Nos. and WO 99/25821; WO 99/61619 and WO 00/17364).

These stacked combinations can be created by any method including, but not limited, to cross breeding plants by any conventional or TOPCROSS™ methodology (DuPont Specialty Grains; Des Moines, IA), CRISPER/Cas, zinc finger nucleases (ZFNs), transcription activator-like effector nucleases (TALENs) or other genetic transformation. If the traits are stacked by genetically transforming the plants, the nucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate expression cassettes (trans) or contained on the same transformation cassette (cis). Expression of the sequences can be driven by the same promoter or by different promoters. In certain instances, it may be desirable to introduce an expression cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, Int'l Patent Application Publication Nos. WO 99/25821; WO 99/25840; WO 99/25853; WO 99/25854 and WO 99/25855.

The nucleotide sequences can be optimized for increased expression in plants. That is, the nucleotide sequences can be synthesized using plant-preferred codons for improved expression. Methods for optimizing nucleotide sequences for expression in plants are well known in the art. See, Campbell & Gowri (1990) *Plant Physiol.* 92:1-11; Murray et al. (1989) *Nucleic Acids Res.* 17:477-498; and Wada et al. (1990) *Nucl. Acids Res.* 18:2367-2411; as well as U.S. Pat. Nos. 5,096,825; 5,380,831; 5,436,391; 5,625,136; 5,670,356 and 5,874,304.

To assist in introducing the nucleotide sequences of interest into the appropriate host cells, the expression cassette can be incorporated or ligated into a vector. As used herein, "vector" refers to a replicon, such as a plasmid, phage or cosmid, to which another nucleic acid segment may be attached so as to bring about the replication of the attached segment. A vector is capable of transferring nucleic acid molecules to the host cells. Bacterial vectors typically can be of plasmid or phage origin.

Typically, the terms "vector construct," "expression vector," "gene expression vector," "gene delivery vector," "gene transfer vector," and "expression cassette" all refer to an assembly that is capable of directing the expression of a sequence or gene of interest. Thus, the terms include cloning and expression vehicles.

Vectors typically contain one or a small number of restriction endonuclease recognition sites where a nucleic acid molecule of interest can be inserted in a determinable fashion without loss of essential biological function of the vector, as well as a selectable marker that can be used for identifying and selecting cells transformed with the vector.

A vector therefore can be capable of transferring nucleic acid molecule to target cells (e.g., bacterial plasmid vectors, particulate carriers and liposomes). The selection of vector will depend upon the preferred transformation technique and the target species for transformation. The most commonly used plant transformation vectors are binary vectors because of their ability to replicate in intermediate host cells such as *E. coli* and *A. tumefaciens*. The intermediate host cells allow one to increase the copy number of the cloning vector and/or to mediate transformation of a different host cell. With an increased copy number, the vector containing the expression cassette of interest can be isolated in significant quantities for introduction into the desired plant. General descriptions of plant vectors can be found, for example, in Gruber et al., "Vectors for plant transformation" 89-119 In: Methods in Plant Molecular Biology & Biotechnology (Glich et al. eds., CRC Press 1993). Examples of vectors for use with *A. tumefaciens* can be found, for example, in U.S. Pat. No. 7,102,057.

Restriction enzymes can be used to introduce cuts into the target nucleic acid molecule (e.g., nucleotide sequence encoding a modified substrate protein and/or NB-LRR protein) and the plasmid to facilitate insertion of the target into the vector such as a plasmid. Moreover, restriction enzyme adapters such as EcoRI/NotI adapters can be added to the target mRNA when the desired restriction enzyme sites are not present within it. Methods of adding restriction enzyme adapters are well known in the art. See, Krebs et al. (2006) *Anal. Biochem.* 350: 313-315; and Lönneborg et al. (1995), supra. Likewise, kits for adding restriction enzyme sites are commercially available, for example, from Invitrogen (Carlsbad, CA).

Alternatively, viruses such as bacteriophages can be used as the vector to deliver the target mRNA to competent host cells. Vectors can be constructed using standard molecular biology techniques as described, for example, in Sambrook & Russell (2001), supra.

Selectable markers can be used to identify and select transformed plants, plant parts or plant host cells. Selectable markers include nucleotide sequences encoding antibiotic resistance, such as those encoding neomycin phosphotransferase II (NEO), hygromycin phosphotransferase (HPT), as well as nucleotide sequences encoding resistance to ampicillin, kanamycin, spectinomycin or tetracycline, and even nucleotide sequences encoding herbicidal compounds such as glufosinate ammonium, bromoxynil, imidazolinones and 2,4-dichlorophenoxyacetate (2,4-D).

Additional selectable markers can include phenotypic markers such as nucleic acid sequences encoding β-galactosidase, β-glucuronidase (GUS; Jefferson (1987) *Plant Mol. Biol. Rep.* 5:387-405); luciferase (Teeri et al. (1989) *EMBO J.* 8:343-350); anthocyanin production (Ludwig et al. (1990) *Science* 247:449-450), and fluorescent proteins such as green fluorescent protein (GFP; Chalfie et al. (1994) *Science* 263:802-805; Fetter et al. (2004) *Plant Cell* 16:215-228; and Su et al. (2004) *Biotechnol. Bioeng.* 85:610-619); cyan fluorescent protein (CYP; Bolte et al. (2004) *J. Cell Science* 117:943-954; and Kato et al. (2002) *Plant Physiol.* 129:913-942), and yellow fluorescent protein (PhiYFP™, available from Evrogen (Moscow, Russia); Bolte et al. (2004) *J. Cell Science* 117:943-954). For additional selectable markers, Bairn et al. (1991) *Proc. Natl. Acad. Sci. USA* 88:5072-5076; Barkley & Bourgeois, "Repressor recognition of operator and effectors" 177-120 In: The Operon (Miller & Reznikoff eds., Cold Spring Harbor Laboratory Press 1980); Bonin (1993) Ph.D. Thesis, University of Heidelberg; Brown et al. (1987) *Cell* 49:603-612; Christopherson et al. (1992) *Proc. Natl. Acad. Sci. USA* 89:6314-6318; Degenkolb et al. (1991) *Antimicrob. Agents Chemother.* 35:1591-1595; Deuschle et al. (1989) *Proc. Natl. Acad. Sci. USA* 86:5400-5404; Deuschle et al. (1990) *Science* 248:480-483; Figge et al. (1988) *Cell* 52: 713-722; Fuerst et al. (1989) *Proc. Natl. Acad. Sci. USA* 86:2549-2553; Gill et al. (1988) *Nature* 334:721-724; Gossen et al. (1992) *Proc. Natl. Acad. Sci. USA* 89:5547-5551; Gossen (1993) Ph.D. Thesis, University of Heidelberg; Hillenand-Wissman (1989) *Topics Mol. Struc. Biol.* 10:143-162; Hlavka et al., *Handbook of Experimental Pharmacology*, Vol. 78 (Springer-Verlag 1985); Hu et al. (1987) *Cell* 48:555-566; Kleinschnidt et al. (1988) *Biochemistry* 27:1094-1104; Labow et al. (1990) *Mol. Cell. Biol.* 10:3343-3356; Oliva et al. (1992) *Antimicrob. Agents Chemother.* 36:913-919; Reines et al. (1993) *Proc. Natl. Acad. Sci. USA* 90:1917-1921; Reznikoff (1992) *Mol. Microbiol.* 6:2419-2422; Yao et al. (1992) *Cell* 71:63-72; Yarranton (1992) *Curr. Opin. Biotech.* 3:506-511; Wyborski et al. (1991) *Nucleic Acids Res.* 19:4647-4653; and Zambretti et al. (1992) *Proc. Natl. Acad. Sci. USA* 89:3952-3956.

The vector therefore can be selected to allow introduction of the expression cassette into the appropriate host cell such as a plant host cell. Bacterial vectors are typically of plasmid or phage origin. Appropriate bacterial cells are infected with phage vector particles or transfected with naked phage vector DNA. If a plasmid vector is used, the cells are transfected with the plasmid vector DNA.

Compositions of the present disclosure also include transformed (transgenic) plant cells, plant parts and plants (i.e., subject plant cells, plant parts or plants) having at least one trait of increased yield, increased root growth, increased waterlogging tolerance, and increased drought tolerance when compared with control/native plant cells, plant parts or plants. Compositions of the present disclosure also include modified plant cells, plant parts and plants (i.e., subject plant cells, plant parts or plants) having at least one trait of increased yield, increased root growth, increased waterlogging tolerance, and increased drought tolerance when compared with control/native plant cells, plant parts or plants, wherein the modification is introduced using gene editing technologies.

The transformed plant cells, plant parts or plants can have at least one nucleic acid molecule, nucleic acid construct, expression cassette or vector having a modified SAUR_FT gene as described herein.

As used herein, "subject plant cell," "subject plant part" or "subject plant" refers to one in which a genetic alteration, such as transformation, has been effected as to a nucleic acid molecule of interest, or is a plant cell, plant part or plant that descended from a plant cell, plant part or plant so altered and that comprises the alteration.

As used herein, "control plant cell," "control plant part" or "control plant" refers to a reference point for measuring changes in phenotype of the subject plant cell, plant part or plant. A control plant cell, plant part or plant can comprise, for example: (a) a wild-type (native) plant cell, plant part or plant (i.e., of the same genotype as the starting material for the genetic alteration that resulted in the subject plant cell, plant part or plant); (b) a plant cell, plant part or plant of the same genotype as the starting material, but which has been transformed with a null construct (i.e., with a construct that has no known effect on the trait of interest, such as a construct comprising a marker gene); (c) a plant cell, plant part or plant that is a non-transformed segregant among progeny of a subject plant cell, plant part or plant; (d) a plant cell, plant part or plant genetically identical to the subject plant cell, plant part or plant, but which is not exposed to conditions or stimuli that would induce expression of the gene of interest; or (e) the subject plant cell, plant part or plant itself, under conditions in which the nucleic acid molecule/construct of interest is not expressed.

Methods of introducing nucleotide sequences into plants, plant parts or plant host cells are well known in the art.

As used herein, "plant cell" or "plant cells" refers to a cell obtained from or found in seeds, suspension cultures, embryos, meristematic regions, callus tissue, leaves, roots, shoots, gametophytes, sporophytes, pollen and microspores. Plant cell also includes modified cells, such as protoplasts, obtained from the aforementioned tissues, as well as plant cell tissue cultures from which plants can be regenerated, plant calli and plant clumps.

As used herein, "plant part" or "plant parts" refers to organs such as embryos, pollen, ovules, seeds, flowers, kernels, ears, cobs, leaves, husks, stalks, stems, roots, root tips, anthers, silk and the like.

As used herein, "plant" or "plants" refers to whole plants and their progeny. Progeny, variants and mutants of the regenerated plants also are included, provided that they comprise the introduced nucleic acid molecule.

As used herein, "grain" means mature seed produced by commercial growers for purposes other than growing or reproducing the species. The class of plants that can be used in the methods described herein is generally as broad as the class of higher plants amenable to transformation techniques, including both monocotyledonous (monocots) and dicotyledonous (dicots) plants.

Examples of plant species of interest herein include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), Macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

Vegetables of interest include, but are not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Ornamentals of interest include, but are not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers of interest include, but are not limited to, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*).

In some instances, the plant cells, plant parts or plants of interest are crop plants (e.g., corn, alfalfa, sunflower, *Brassica*, soybean, cotton, safflower, peanut, *sorghum*, wheat, millet, tobacco, etc.).

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Methods of the present disclosure include introducing and expressing in a plant cell, plant part or plant a nucleic acid molecule or construct as described herein. As used herein, "introducing" refers to presenting to the plant cell, plant part or plant, a nucleic acid molecule or construct in such a manner that it gains access to the interior of a cell of the plant. The methods do not depend on the particular method for introducing the nucleic acid molecule or nucleic acid construct into the plant cell, plant part or plant, only that it gains access to the interior of at least one cell of the plant or plant part. Methods of introducing nucleotide sequences, selecting transformants and regenerating whole plants, which may require routine modification in respect of a particular plant species, are well known in the art. The methods include stable transformation methods, transient transformation methods, virus-mediated methods and sexual breeding. As such, the nucleic acid molecule or construct can be carried episomally or integrated into the genome of the host cell.

Methods of the present disclosure include introducing modifications to the promoter, 5'-untranslated region, coding region, 3'-untralted region of the SAUR_FT gene using gene editing technologies. Suitable gene editing technologies include, for example, CRISPR (clustered regularly interspaced short palindromic repeats) technologies including CRISPR/Cas9 and CRISPR/Cpf1, zinc finger nuclease gene editing technologies, and TALEN (transcripton activator-like effector nuclease) gene editing technologies.

As used herein, "stable transformation" means that the nucleic acid molecule or construct of interest introduced into the plant integrates into the genome of the plant and is capable of being inherited by the progeny thereof. As used herein, "transient transformation" means that the nucleic acid molecule or construct of interest introduced into the plant is not inherited by progeny.

Methods of transforming plants and introducing a nucleotide sequence of interest into plants can and will vary depending on the type of plant, plant part or plant host cell (i.e., monocotyledonous or dicotyledonous) targeted for transformation. Methods of introducing nucleotide sequences into plant host cells therefore include *Agrobacterium*-mediated transformation (e.g., *A. rhizogenes* or *A. tumefaciens*; U.S. Pat. Nos. 5,563,055 and 5,981,840), calcium chloride, direct gene transfer (Paszkowski et al. (1984) *EMBO J.* 3:2717-2722), electroporation (Riggs et al. (1986) *Proc. Natl. Acad. Sci. USA* 83:5602-5606), microinjection (Crossway et al. (1986) *Biotechniques* 4:320-334), microprojectile bombardment/particle acceleration (McCabe et al. (1988) *Biotechnology* 6:923-926; and Tomes et al., "Direct DNA transfer into intact plant cells via microprojectile bombardment" In: Plant Cell, Tissue, and Organ Culture: Fundamental Methods (Gamborg & Phillips eds., Springer-Verlag 1995); as well as U.S. Pat. Nos. 4,945,050; 5,879, 918; 5,886,244 and 5,932,782), polyethylene glycol (PEG), phage infection, viral infection, and other methods known in the art. See also, EP Patent Nos. 0 295 959 and 0 138 341.

A nucleic acid molecule or construct as described above herein can be introduced into the plant cell, plant part or plant using a variety of transient transformation methods. Methods of transiently transforming plant cells, plant parts or plants include, but are not limited to, *Agrobacterium* infection, microinjection or particle bombardment. See, Crossway et al. (1986) *Mol. Gen. Genet.* 202:179-185; Hepler et al. (1994) *Proc. Natl. Acad. Sci. USA* 91:2176-2180; Hush et al. (1994) *J. Cell Sci.* 107:775-784; and Nomura et al. (1986) *Plant Sci.* 44:53-58. Alternatively, the plant cell, plant part or plant can be transformed by viral vector systems or by precipitation of the nucleic acid molecule or construct in a manner that precludes subsequent release of the DNA. Thus, transcription from the particle-bound nucleotide sequence can occur, but the frequency with which it is released to become integrated into the genome is greatly reduced. Such methods include the use of particles coated with polyethylimine (PEI; Sigma; St. Louis, MO).

Likewise, the nucleic acid molecules or constructs as described herein can be introduced into the plant cell, plant part or plant by contacting it with a virus or viral nucleic acids. Generally, such methods involve incorporating the nucleic acid molecule or construct within a viral DNA or RNA molecule. It is recognized that the nucleotide sequences can be initially synthesized as part of a viral polyprotein, which later can be processed by proteolysis in vivo or in vitro to produce the desired recombinant protein. Methods for introducing nucleotide sequences into plants and expressing the protein encoded therein, involving viral DNA or RNA molecules, are well known in the art. See, Porta et al. (1996) *Mol. Biotechnol.* 5:209-221; as well as U.S. Pat. Nos. 5,866,785; 5,889,190; 5,889,191 and 5,589, 367.

Methods also are known in the art for the targeted insertion of a nucleic acid molecule or construct at a specific location in the plant genome. In some instances, insertion of the nucleic acid molecule or construct at a desired genomic location can be achieved by using a site-specific recombination system. See, Int'l Patent Application Publication Nos. WO 99/025821, WO 99/025854, WO 99/025840, WO 99/025855 and WO 99/025853.

Transformation techniques for monocots therefore are well known in the art and include direct gene uptake of exogenous nucleic acid molecules or constructs by protoplasts or cells (e.g., by PEG- or electroporation-mediated uptake, and particle bombardment into callus tissue). Transformation of monocots via *Agrobacterium* also has been described. See, Int'l Patent Application Publication No. WO 94/00977 and U.S. Pat. No. 5,591,616; see also, Christou et al. (1991) *Bio/Technology* 9:957-962; Datta et al. (1990) *Bio/Technology* 8:736-740; Fromm et al. (1990) *Biotechnology* 8:833-844; Gordon-Kamm et al. (1990) *Plant Cell*

2:603-618; Koziel et al. (1993) *Bio/Technology* 11:194-200; Murashige & Skoog (1962) *Physiologia Plantarum* 15:473-497; Shimamoto et al. (1989) *Nature* 338:274-276; Vasil et al. (1992) *Bio/Technology* 10:667-674; Vasil et al. (1993) *Bio/Technology* 11:1553-1558; Weeks et al. (1993) *Plant Physiol.* 102:1077-1084; and Zhang et al. (1988) *Plant Cell Rep.* 7:379-384; as well as EP Patent Application Nos. 0 292 435; 0 332 581 and 0 392 225; Int'l Patent Application Publication Nos. WO 93/07278 and WO 93/21335; and U.S. Pat. No. 7,102,057.

Transformation techniques for dicots also are well known in the art and include *Agrobacterium*-mediated techniques and techniques that do not require *Agrobacterium*. Non-*Agrobacterium*-mediated techniques include the direct uptake of exogenous nucleic acid molecules by protoplasts or cells (e.g., by PEG- or electroporation-mediated uptake, particle bombardment, or microinjection). See, Klein et al. (1987) *Nature* 327:70-73; Paszkowski et al. (1984) *EMBO J.* 3:2717-2722; Potrykus et al. (1985) *Mol. Gen. Genet.* 199: 169-177; and Reich et al. (1986) *Bio/Technology* 4:1001-10041; as well as U.S. Pat. No. 7,102,057.

Plant cells that have been transformed can be grown into plants by methods well known in the art. See, McCormick et al. (1986) *Plant Cell Rep.* 5:81-84. These plants then can be grown, and either pollinated with the same transformed strain or different strains, and the resulting progeny having the desired phenotypic characteristic identified. Two or more generations can be grown to ensure that expression of the desired phenotypic characteristic is stably maintained and inherited, and then seeds harvested to ensure expression of the desired phenotypic characteristic has been achieved.

Compositions, systems and methods are provided for conferring at least one trait of increased yield, increased root growth, increased waterlogging tolerance, and increased drought tolerance by modifying a gene encoding small auxin upregulated protein flooding tolerance (SAUR_FT). Briefly, the compositions, systems and methods are based upon modifying the 5'-untranslated region of SAUR_FT. As used herein, small auxin upregulated protein flooding tolerance (SAUR_FT) refers to SAUR_FT from Glycine max (soybean), homologs of SAUR_FT, and orthologs of SAUR_FT.

As used herein, "waterlogging" refers to a condition where the root system of a plant is fully submerged (soil fully saturated), but above-ground organs of the plant are in air. Increased waterlogging tolerance can include plant survival strategies relating to aeration of root tissue and changes in root architecture such as development of aerenchyma, establishment of suberized exodermis, development of shallow and adventitious (shoot borne) roots, and combinations thereof.

The methods described herein include introducing into a plant cell, a plant part or a plant at least one nucleic acid molecule, construct, expression cassette or vector as described herein to confer at least one trait of increased yield, increased root growth, increased waterlogging tolerance, and increased drought tolerance by modifying a gene encoding small auxin upregulated protein flooding tolerance (SAUR_FT).

In one aspect, the present disclosure is directed to a plant comprising at least one of a modified 5'-untranslated region of small auxin upregulated protein flooding tolerance (SAUR_FT) gene, a modified 5'-untranslated region of SAUR_FT gene homolog, and a SAUR_FT gene ortholog. In one embodiment the plant is a transgenic plant.

The modified 5'-untranslated region of the SAUR_FT gene comprises a poly-A insertion. Suitably, the poly-A insertion is at least an 11 base pair nucleotide insertion.

The plant includes at least one trait of increased yield, increased root growth, increased waterlogging tolerance, and increased drought tolerance as compared to a plant not having the modified 5'-untranslated region of small auxin upregulated protein flooding tolerance (SAUR_FT) gene, the modified 5'-untranslated region of SAUR_FT gene homolog, and the SAUR_FT gene ortholog.

The plant includes about 1.5-fold to about 2-fold more adventitious/aerial roots than a plant not comprising the modified 5'-untranslated region of the SAUR_FT gene.

Suitable plants are crop plants.

In another aspect, the present disclosure is directed to a seed of the plant.

In another aspect, the present disclosure is directed to a plant cell of the plant.

In another aspect, the present disclosure is directed to a progeny of the plant.

In another aspect, the present disclosure is directed to a method of selecting a plant having at least one of increased root system architecture, increased waterlogging tolerance, increased drought tolerance, increased yield, and combinations thereof, the method comprising obtaining a sample of the plant and analyzing small auxin upregulated protein flooding tolerance (SAUR_FT) gene.

The method can further include determining if the plant includes at least one of increased root system architecture, increased waterlogging tolerance, increased drought tolerance, and combinations thereof when the SAUR_FT gene 5'-untranslated region comprises a poly-A insertion.

The method can further include analyzing the SAUR_FT gene 5'-untranslated region.

The method can further include determining if the plant has at least one of increased root system architecture, increased waterlogging tolerance, increased drought tolerance, and combinations thereof when the SAUR_FT gene 5'-untranslated region comprises a poly-A insertion.

Suitably, the poly-A insertion is at least an 11 base pair nucleotide insertion.

The method can further include contacting the sample with an agent that specifically binds to a SAUR_FT nucleic acid sequence. Suitable SAUR_FT nucleic acid sequences include, for example, a SAUR_FT gene sequence, a SAUR_FT DNA sequence, and a SAUR_FT RNA sequence. The method can further include contacting the sample with an agent that specifically binds to a SAUR_FT protein. Suitable agents that specifically bind to SAUR_FT include for example, a nucleic acid that is complementary to a SAUR_FT gene sequence, a SAUR_FT DNA sequence, and a SAUR_FT RNA sequence. Suitable agents that specifically bind to SAUR_FT protein include antibodies, for example. The plant can be selected by determining a reduced expression of SAUR_FT as compared to expression of SAUR_FT in a wildtype/native plant. A plant can be selected for at least one of an increased root system architecture, an increased waterlogging tolerance, an increased drought tolerance, and combinations thereof, based on the presence of a sequence located at about 1 to about 780 bp nucleotides from the initiation start site using Gene ID Glyma 03G029600 as a reference sequence. The insertion can be a poly A nucleic acid insertion. Suitably, the insertion can be at least an 11 bp insertion.

In another aspect, the present disclosure is directed to a method of producing a plant including at least one of an increased root system architecture, an increased waterlogging tolerance, an increased drought tolerance, and combinations thereof, the method comprising: reducing expression of small auxin upregulated protein flooding tolerance (SAU- R_FT) gene. In one embodiment the plant is a transgenic plant. In another embodiment, the plant is produced using a gene editing technology.

Suitably, the expression of the SAUR_FT gene can be reduced by modifying the SAUR_FT gene 5'-untranslated region. The SAUR_FT gene 5'-untranslated region can be modified by creating an insertion in the SAUR_FT gene 5'-untranslated region. Suitably, the insertion is created at a site located about 1 to about 780 bp nucleotides from the initiation start site. The initiation start site can be determined using Gene ID Glyma 03G029600 as a reference gene sequence.

The insertion can include a poly-A insertion. Suitably, the insertion can be at least an 11 base pair nucleotide insertion.

EXAMPLES

Materials and Methods
Plant Materials and Waterlogging Test

Figure 11:
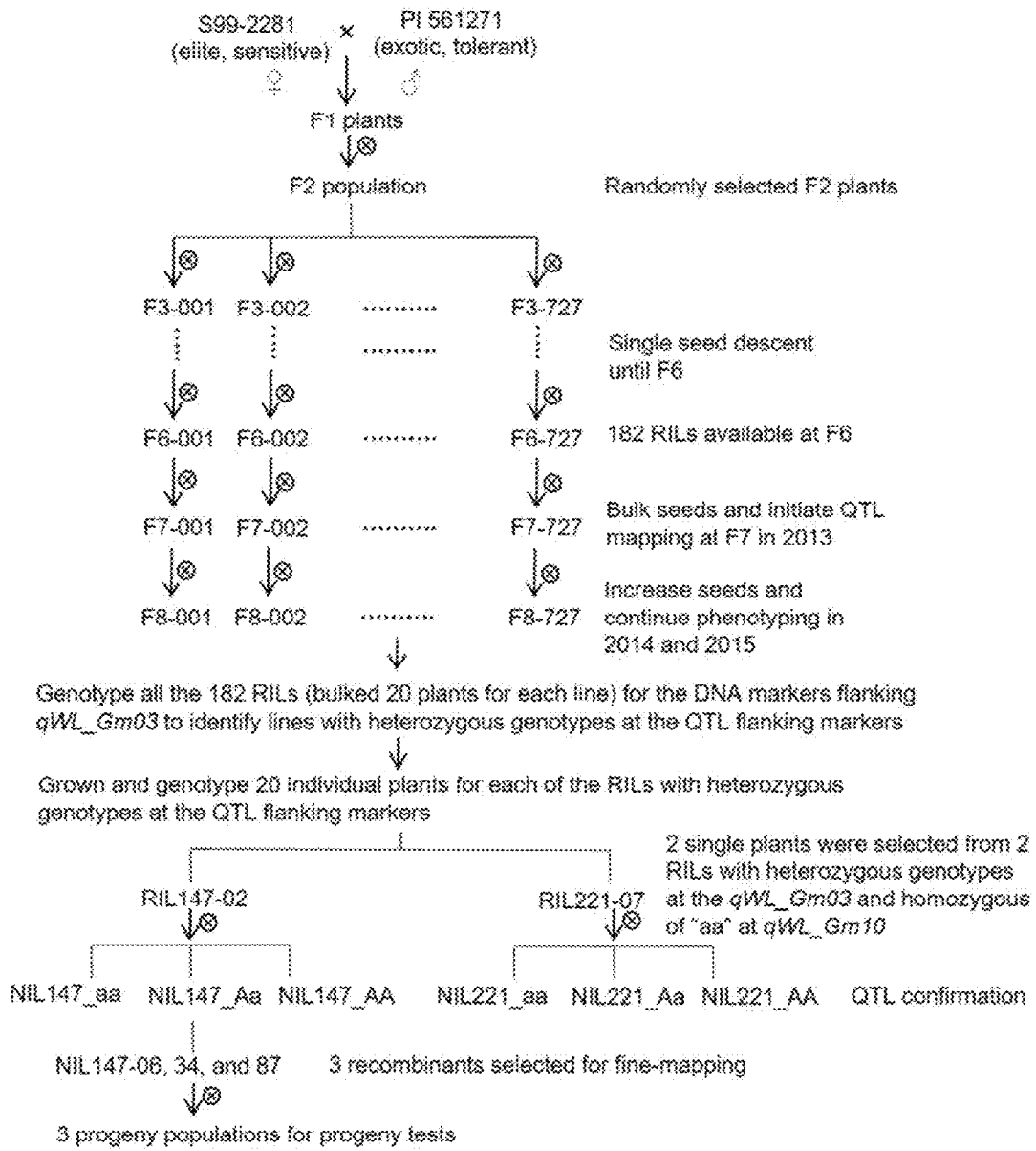
FIG. 11 depicts the breeding scheme to develop recombinant inbred line population and near isogenic lines (NILs) for qWL_Gm03. "a" and "A" stand for alleles of qWL_Gm03 from S99-2281 and PI 561271, respectively.

A soybean mapping population was developed from a S99-2281×PI 561271 cross, from which plants were randomly selected and advanced via single-seed descent to produce 182 F7-derived recombinant inbred lines (RILs) (FIG. 11). The RILs were advanced one more generation to increase seeds in the field of Delta Research Center (DRC) of the University of Missouri, Portageville, MO Near isogenic lines (NILs) for qWL_Gm03 were identified from heterogeneous inbred families at F8 generation (FIG. 11). Two single F8 plants, which have heterozygous genotypes at the qWL_Gm03 region, were selected from RIL147 and RIL221 families Two sets of NILs (NIL147_aa/AA and NIL221_aa/AA) were selected in the progeny populations of these two F8 plants. Three recombinants with crossover in the candidate region of qWL_Gm03 were selected from the progeny population of NIL147_Aa for fine-mapping of qWL_Gm03 (FIG. 11).

Waterlogging test were performed in both field and greenhouse. Field tests for RIL populations and fine-mapping were conducted at the Lee Farm at the DRC in Portageville, MO The evaluation of NILs were performed at four locations, including DRC (MO), Rhower Research Station (AR), Delta Research and Extension Center (MS) and Red River Research Station (LA). The soil types of the four locations were Sharkey clay (very fine, smectitic, thermic Chromic Epiaquerts). Each lines were planted in hill plots at a density of 8 seeds per plot with 1 meter spacing with 2 to 3 replications. Waterlogging treatments were imposed by flood irrigation. Water was pumped on the field when 80% of the lines within each maturity block were at the R1 growth stage (Fehr and Caviness 1977). The water was raised to 5 to 10 cm above the soil surface and kept at this level for 4 to 6 days depending on when severe injury began to show within each maturity block after which water was allowed to drain from the field. Plants were allowed to recover for 2 weeks. Each line was rated from 1 to 5 for a flooding injury score (FIS), in which 1 indicated no apparent injury and 5 indicated most plants severely injured or dead. Greenhouse tests were conducted in soil cones with turface and sand (2:1 ratio) (30 cm deep, 5 cm in diameter) for the early vegetative stage and soil pots with field soil and Promix (1:1 ratio) (30 cm deep, 20 cm in diameter) for the early reproductive stage. Waterlogging treatments were imposed by keeping water of 5 to 10 cm above the soil surface and kept at this level for 14 d. Plants were allowed to recover for 1 week before scoring for FIS.

Linkage Map Construction and QTL Analysis

Genomic DNA of the parents and the 182 Fs RILs was extracted using a standard CTAB method (Doyle & Doyle 1987). Single nucleotide polymorphism (SNP) genotyping was performed at the Washington University in St. Louis by using the SoySNP6K Illumina Infinium BeadChips (Illumina, Inc. San Diego, CA). The SNP alleles were called using the GenomeStudio Genotyping Module (Akond et al. 2013; Song et al. 2013). A SNP linkage map was constructed using the program JoinMap 3.0 (van Ooijen & Voorrips 2001). A LOD score of 3.0 was used for two-point analysis and a LOD score of 2.0 was used for all three-point and multipoint analysis. Putative QTL for the traits studied were initially detected by the interval mapping method using the program MapQTL 5.0 (van Ooijen 2004). Composite interval mapping (CIM) was then performed using the multi-QTL method and the appropriate cofactors (van Ooijen & Voorrips 2001). A LOD score significance threshold value was estimated for each trait in each location by 1,000 permutation to determine a QTL at the genome wide significance level of $P=0.05$ (Doerge & Churchill 1996).

Marker-Trait Association Analysis and Estimation of Genetic Effects

The marker-trait association and estimation of genetic effects followed previous reports (Ye et al. 2015). Linear correlation analysis was used to determine the marker-trait associations in progeny populations. Genotypes for a marker locus were coded as i (i=1, 2 and 3 for S99-2281-like homozygote, heterozygote, and PI 561271-like homozygote, respectively) for the correlation analysis. Additive and dominance effects of the locus on germination or plant height were estimated using the linear regression model: $y_{ij}=\mu+\alpha x+dz+\varepsilon_{ij}$, where $y_{ij}$ was the trait value for the jth plant of the ith marker genotype; $\mu$ was the model mean; x was the dummy variable for the additive component and was coded as −1, 0 and 1 for i=1, 2 and 3, respectively; z was the dummy variable for the dominance component and was coded as 0.5, 0 or 0.5 for i=1, 2 or 3; a and d were regression coefficients and estimates of the additive and dominance effects, respectively; and $\varepsilon_{ij}$ was the error term of the model. Correlation and regression analyses were implemented using SAS program (SAS Institute 2011).

Phenotyping for Root Traits

In the greenhouse, soybean roots were phenotyped as described in Prince et al., 2015. Roots were sampled and cleaned from soil cones or soil pots. Then root samples were transferred into water-filled clear trays to carefully remove turface, soil or Promix particles firmly attached to the root. The roots were then transferred into another water-filled tray, scanned using an Epson Scanner 10000XL (Epson America Inc., CA, USA) and analyzed using WinRhizo Pro software (Regent Instruments Inc., Canada). Data on total root length and root tip numbers were derived from the imaging analysis. In the field, soybean roots were sampled at the R5 growth stage using the "shovelomics" method (Trachsel et al. 2011). Three images for each root were taken at an interval of 120°. The images were analysis by "DIRT" and data was averaged for the three images (Bucksch et al. 2014; Das et al. 2015).

Tests of Water Potential and Water Content of Soybean Plants

Shoots of plants (above-ground tissues) were weighed immediately after harvesting and then dried at 105° C. for 3 days to measure dry weight to calculate the water content. Leaf water potential was measured with a pressure chamber (Model 610 Pressure Chamber Instrument, PMS Instrument Co., Albany, OR, USA) on fully matured leaves from the upper canopy as described by Boyer & Ghorashy 1971.

Inheritance and QTL for Waterlogging Tolerance in the Cultivar-Exotic Cross

A RIL population (182 $F_7$ lines) was developed by crossing S99-2281 (elite, waterlogging sensitive) with PI 561271 (exotic, waterlogging tolerant) (FIG. 11). Flooding injury scores (FIS) were used to represent waterlogging tolerance levels and FIS were rated from 1 to 5 with 1=no apparent injury and 5=most plants severely injured or dead (FIG. 1A). The field evaluation of the RIL population observed transgressive segregation in FIS for all three years (FIG. 1B), indicating that both parents should have donor locus or loci for waterlogging tolerance. FIS from 2013 and 2014 showed normal distributions; while FIS from 2015 were accumulated towards the sensitive side. The different distribution pattern of FIS from 2015 was caused by prolonged flooding period due to an unexpected heavy rain during flooding recovery time. However, high broad-sense heritability ($H^2$=0.50) on FIS was detected across three years (FIG. 1B), suggesting the genetic factors segregating in the RIL population are stable and can be detected.

Linkage maps for the RIL population was constructed using 1,797 SNP markers acquired from SoySNP6K Illumina Infinium BeadChips genotyping with an average genetic interval of 1.47 cM (Table 2).

Figure 1B:
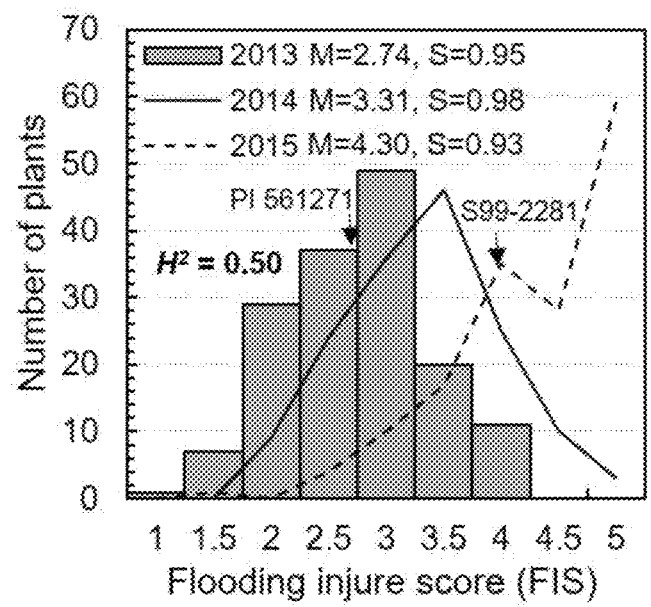

The subsequent QTL analysis identified two novel loci associated with FIS on Chr. 3 and 10 and named as qWL_Gm03 and qWL_Gm10, respectively (FIG. 2). qWL_Gm03 was detected in all three years of field evaluation and qFT_Gm10 was only detected in 2013 and 2014, possibly due to shifted phenotypic distribution pattern in 2015 (FIG. 1B). The donor allele of qWL_Gm03 was from the exotic parent (PI 561271) and the donor allele of qWL_Gm10 was from the elite parent (S99-2281) (Table 1), which explained the observed transgressive distributions of FIS (FIG. 1B). qWL_Gm03 had a relatively major effect in waterlogging tolerance, as it was consistently mapped on the same chromosomal region in all three independent years, explaining 16.9% to 33.1% of phenotypic variations (Table 1). qWL_Gm10 explained relatively minor effects with varied phenotypic contributions of to 15.4% and 8.5% in 2013 and 2014, respectively.

TABLE 2

Information of the constructed linkage maps for the RIL population.

| Chr. | Number of markers | Length (cM) | Average interval (cM) |
|---|---|---|---|
| 1 | 90 | 114.9 | 1.29 |
| 2 | 125 | 133.3 | 1.08 |
| 3 | 84 | 114.9 | 1.38 |
| 4 | 89 | 136.4 | 1.55 |
| 5 | 81 | 109.2 | 1.37 |
| 6 | 112 | 171.8 | 1.55 |
| 7 | 112 | 133.6 | 1.20 |
| 8 | 112 | 173.9 | 1.57 |
| 9 | 89 | 130.4 | 1.48 |
| 10 | 84 | 138.7 | 1.67 |
| 11 | 73 | 139.1 | 1.93 |
| 12 | 78 | 127.4 | 1.65 |
| 13 | 67 | 89.8 | 1.36 |
| 14 | 104 | 120.0 | 1.17 |
| 15 | 81 | 113.0 | 1.41 |
| 16 | 102 | 103.5 | 1.02 |
| 17 | 89 | 126.0 | 1.43 |
| 18 | 108 | 147.4 | 1.38 |
| 19 | 67 | 82.2 | 1.25 |
| 20 | 50 | 130.4 | 2.66 |
| Summary | 1797 | 2535.9 | 1.47 |

TABLE 1

Summary of QTL associated with flooding injury score (FIS) mapped in the RIL mapping population.

| QTL | Year | Chro. | Nearest marker[a] | $a$[b] | $R_2$ (%)[c] | Donor[d] |
|---|---|---|---|---|---|---|
| qWL_Gm03 | 2013 | 3 | Gm03_3087237_A/G | −0.27 | 18.1 | PI 561271 |
|  | 2014 | 3 | Gm03_3087237_A/G | −0.39 | 33.1 | PI 561271 |
|  | 2015 | 3 | Gm03_3225968_G/A | −0.28 | 16.8 | PI 561271 |
| qWL_Gm10 | 2013 | 10 | Gm10_43840376_T/C | 0.26 | 15.4 | S99-2281 |
|  | 2014 | 10 | Gm10_43107961_A/G | 0.20 | 8.5 | S99-2281 |

Figure 2:
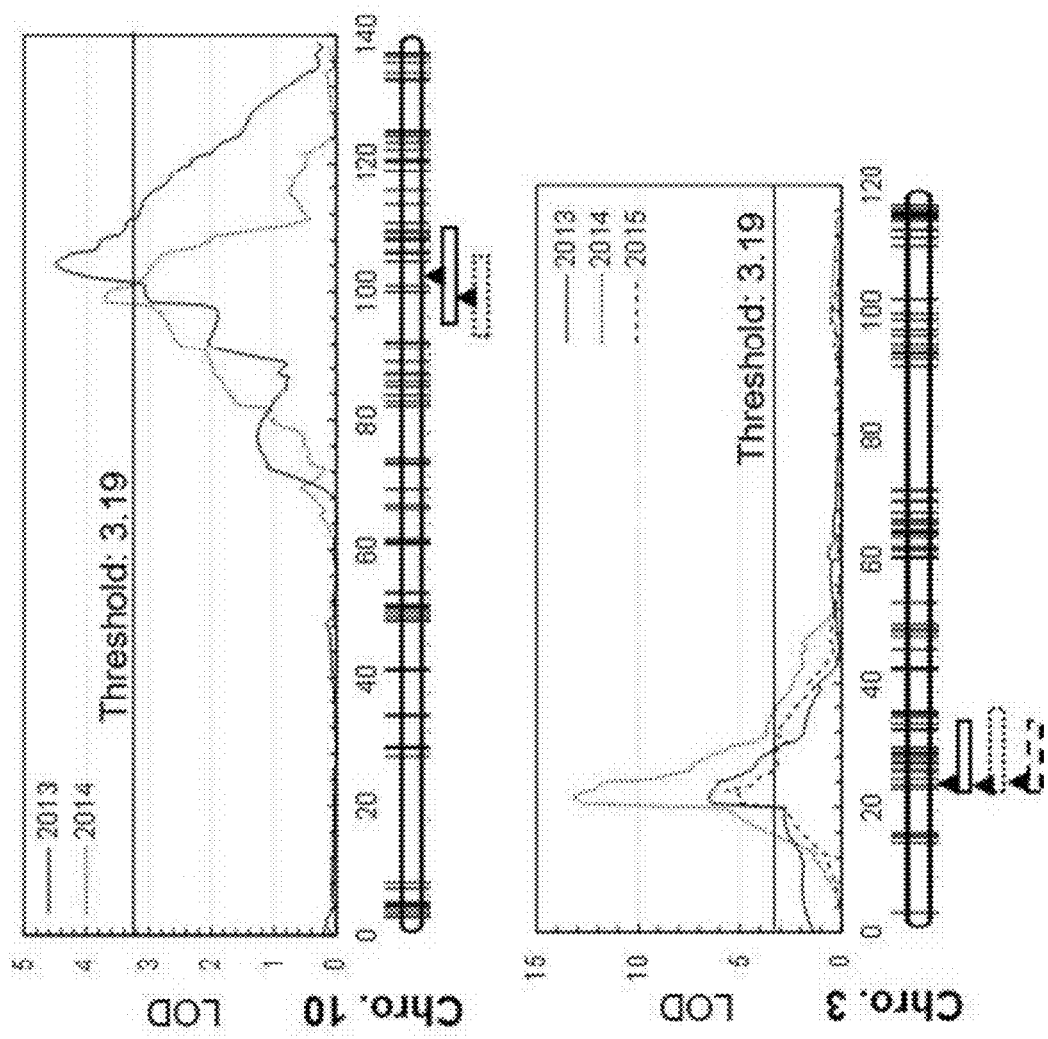
FIG. 2 depicts chromosomal locations of the two QTL associated with flooding injury scores (FIS) and the distributions of LOD of the QTL analysis. qWL_Gm03 is shown at the left and qWL_Gm10 is shown at the right. The linkage maps were constructed based on genotyping results from Illumina 6K SNP arrays using JoinMap 4.0 (Supplementary Table 1). The likely-hood (LOD) value were generated using MapQTL 5.0 and the threshold was calculated by 1,000 permutations. The bars flank the candidate region of the QTL for each year and the arrows point at the peaks of the corresponding QTL for each year.

[a]The nearest maker to the peak position of the LOD distribution in FIG. 2. The marker positions were based on soybean genome assembly of Wm82.a1.v1.1.
[b]The additive effect of the QTL in the respective years.
[c]The percentage of contributions of the QTL to the total phenotypic variations within each year.
[d]The parent, from which the favorable alleles for waterlogging tolerance of the QTL come Genetic Component Effects of the Isolated Major QTL qWL_Gm03

Figure 3A:
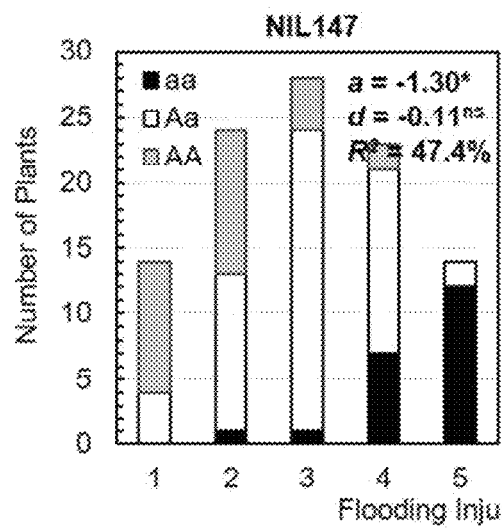
FIGS. 3A-3D depict genetic effects of qWL_Gm03 on waterlogging tolerance at the near isogenic backgrounds. Phenotypic distribution and genetic effects of qWL_Gm03 in the progeny populations derived from NIL147_Aa (a) and NIL221_Aa (b), respectively. Progeny populations for NIL147_Aa and NIL221_Aa were developed by self-pollination (FIG. 11) containing 82 and 100 plants for each population, respectively. Flooding injury scores (FIS) were taken at the early vegetative stage (R1 to R2) in the field. Individual plants were genotyped by nearest marker (Gm03_3087237_A/G) of qWL_Gm03. Additive effects (a), dominance effects (d), and proportion of the variance explained by the QTL ($R^2$) were estimated based on Model 1, with a significant value (* for P<0.0001 and ns for P=0.05 or greater) indicating that the PI 561271-derived allele on the marked heterozygous region reduced FIS. A positive or negative value indicates that the parental allele "A" or "a" contributed an effect-increasing FIS. (c) Waterlogging tolerance test of the NILs at early vegetative stage in the greenhouse. Then plants of each NIL were grown in 40 cm cones and subjected to waterlogging stress at V2 growth stage for 10 days. Flooding injury scores (FIS) were evaluated at 10 days after removing waterlogging stress. (d) Waterlogging tolerance test of the NILs at early reproductive stage in the field. Five plants of each NIL were grown in the field at multiple states in the US (MO: Missouri, AR: Arkansas, MS: Mississippi, and LA: Louisiana) and subjected to waterlogging stress at R1 to R2 growth stage for 5 days. Flooding injury scores were evaluated at 10 days after removing waterlogging stress. Columns and bars represent means and standard deviations of FIS of three biological replicates for each NIL at each location. Significant differences in FIS between "aa" and "AA" were observed at each location (P<0.001, Student's-t-test).
Figure 3B:
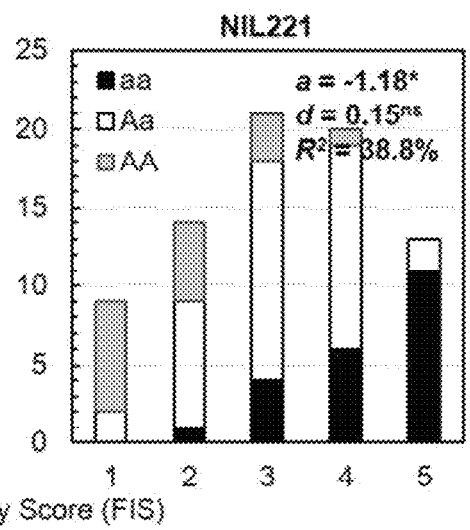

Two sets of NILs (NIL147 and NIL221) were identified from the heterogeneous inbred families (F8:9) by screening the QTL associated SNP markers (FIG. 11). Two single plants (RIL147_02 and RIL221_07) with heterozygous genotypes at the qWL_Gm03 region were selected from two families to advance to $F_9$ (FIG. 11). The two $F_9$ populations segregating qWL_Gm03 were used to evaluate the genetic component effects of the QTL. Normal distributions were observed in the two $F_9$ populations with clear different distribution patterns for plants with three different genotypes (aa, Aa and AA) at qWL_Gm03 (FIGS. 3A & 3B). Significant additive effects of qWL_Gm03 were identified at the NIL backgrounds with phenotypic contributions of 47.4% and 37.8% in NIL147 and NIL221, respectively (FIGS. 3A & 3B). However, dominance effects were not significant for qWL_Gm03 (FIGS. 3A & 3B), indicating that this QTL plays dosage effects in waterlogging tolerance.

Figure 3C:
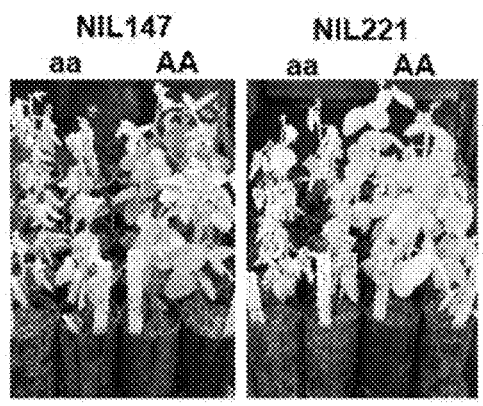
Figure 3D:
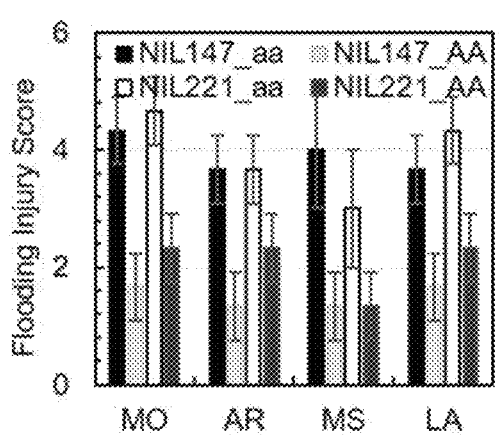

Two sets of NILs were selected as NIL147 aa/AA and NIL221 aa/AA from the two $F_9$ populations (FIG. 11). The NILs with tolerant allele "A" showed obvious stronger waterlogging tolerance than the NILs with the sensitive allele "a" at the early vegetative stage in the greenhouse (FIG. 3C). The two sets of NILs were further evaluated for waterlogging tolerance at the early vegetative stage at four field locations across Mid-South of US. As expected, the tolerant allele "A" can greatly improve waterlogging tolerance of soybean plants compared to the sensitive allele "a" across all four field locations (FIG. 3D). These results not only confirmed the genetic effects of qWL_Gm03 in waterlogging tolerance, but also exhibited that qWL_Gm03 had potential to be adapted at different environments to improve waterlogging tolerance of soybean cultivars.

Fine-Mapping Narrowed the Candidate Region for qWL_Gm03

Figure 4:
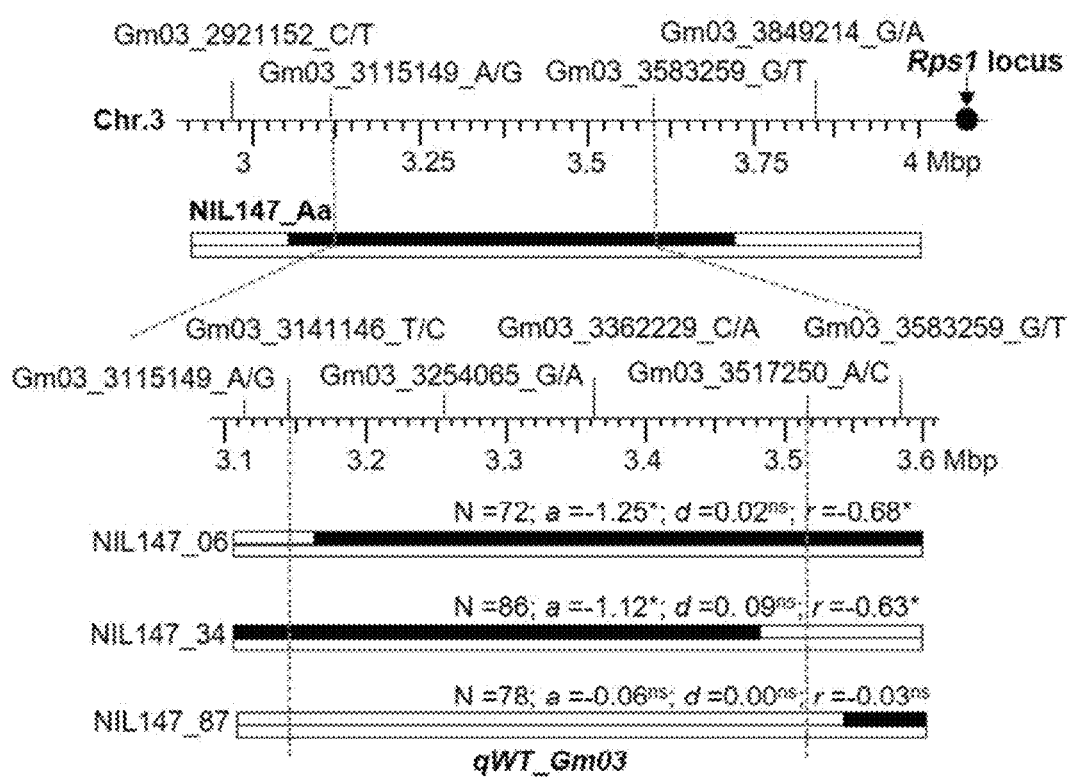
FIG. 4 depicts fine mapping of the qWL_Gm03 region. Markers on the partial map of chromosome 3 were aligned against the Williams 82 genome sequence and used to select recombinants (NIL147_06, 34 and 87) to dissect the initial introgression segment from PI 567271 (black bar in the top panel) in the EM93-1 background (empty bars). N, the number of plants in a recombinant-derived progeny populations; r, marker-trait correlation coefficients for Flooding Injury Scores (FIS), with a significant value (* for P<0.0001 and ns for P=0.05 or greater) indicating that the PI 561271-derived allele on the marked heterozygous region reduced FIS. Vertical dash lines delimit qWL_Gm03, based on the progeny tests. The SNP markers were designed in Kompetitive Allele Specific PCR assay. The marker positions are based on soybean genome assembly Wm82.a2.v1.

Three recombinants with crossovers between the flanking markers of qWL_Gm03, were selected from the $F_9$ population derived from RIL147-02 for progeny test (FIG. 11). Partial physical map was constructed using six SNP markers, which were developed based on the sequence alignment of the QTL interval regions (Valliyodan et al. 2016). The three recombinants were genotyped by these SNP markers to determine the points of chromosome crossovers (FIG. 4). Progeny populations were developed containing 72 to 86 self-pollinated plants for these three recombinants in the waterlogging test field. Each progeny plant was genotyped by the DNA markers (Gm03_3362229_C/A or Gm03_3583259_G/T) that were segregating in the respective populations and phenotyped using FIS at the early reproductive stage (FIG. 4). Marker-trait correlations were significant only in the NIL147-06 and -34 progeny populations, with r=-0.63 to -0.68 for FIS. Meanwhile, genetic analysis confirmed the significant additive effect of qWL_Gm03 in these two progeny populations. The similar strength of correlation and additive effects in the two progeny populations suggests that qWL_Gm03 locates on the respective heterozygous regions of the recombinants: NIL147-06 and -34, which narrows the qWL_Gm03-containing interval of <380-Kbp between Gm03_3141146_T/C and Gm03_3517250_A/C containing 30 predicted genes (FIG. 4). The absence of marker-trait association and significant additive effect of the QTL in the progeny population of NIL147-87 confirmed the qWL_Gm03-containing interval and excluded genomic region downstream of Gm03_3517250_A/C. Previously, a locus (Rps1) conferring resistance to *Phytophthora* root rot caused by *Phytophthora sojae* was mapped near the qWL_Gm03 region (Gao & Bhattacharyya 2008; Cheng et al. 2017). Based on the fine-mapping results, this resistance locus is excluded from the candidate region of qWL_Gm03 (FIG. 4).

Figure 5A:
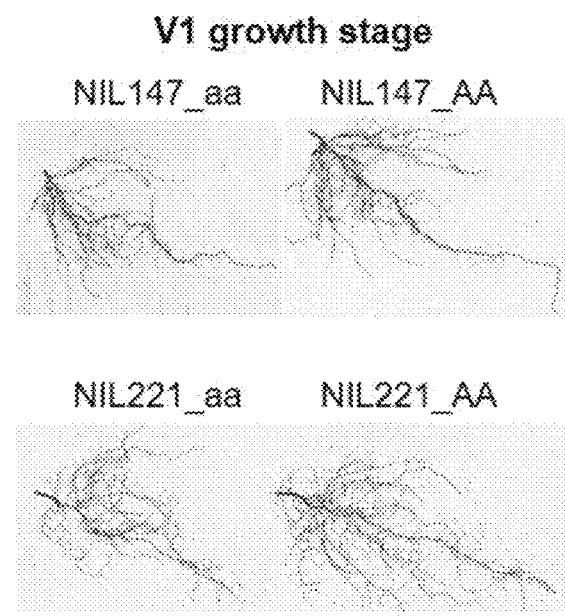
FIGS. 5A-5D depict genotypic differences in root growth among NILs. (a) Representative images of roots of NILs at V1 growth stage. "aa" stands for the NILs with the sensitive allele from S99-2281 and "AA" stands for the NILs with the tolerant allele from PI 561271. Effects of qFT_Gm03 on total root length (b) and root tip numbers (c) during waterlogging treatment. The two sets of NILs (NIL147: left and NIL221: right) were planted in turface and sand (2:1 ratio) and grown in the greenhouse. Waterlogging stress was added to plants at V1 growth stage. "C" stands for the control conditions without waterlogging stress and "WL" stands for waterlogging treatment. The scanned images of roots were analyzed using WinRhizo Pro software. Dots and bars represent the means and standard errors of each data point calculated based 10 biological replicates. (d) Effects of qWL_Gm03 on induction of adventitious roots by waterlogging. Two sets of NILs were planted in the soil pots in greenhouse. Waterlogging stress was applied to plants at V1 growth stage and the induced adventitious roots were counted at 7 days after the treatment. Data shown are means±standard deviations of 20 plants for each line. Student's-t-test was used to compare means between NIL147/221_aa and NIL147/221_AA, respectively.
Figure 5B:
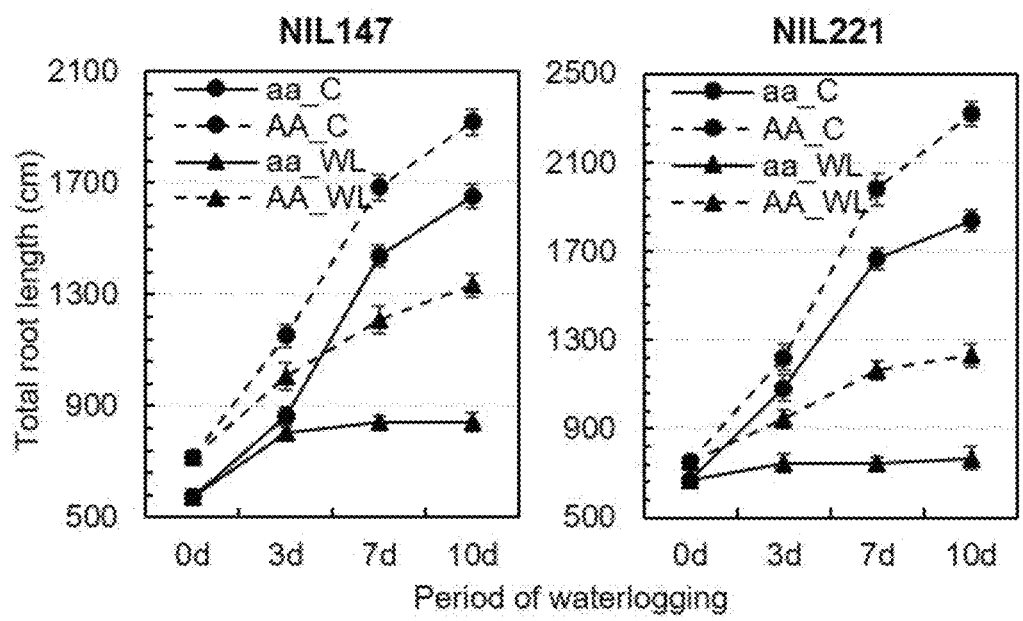
Figure 5C:
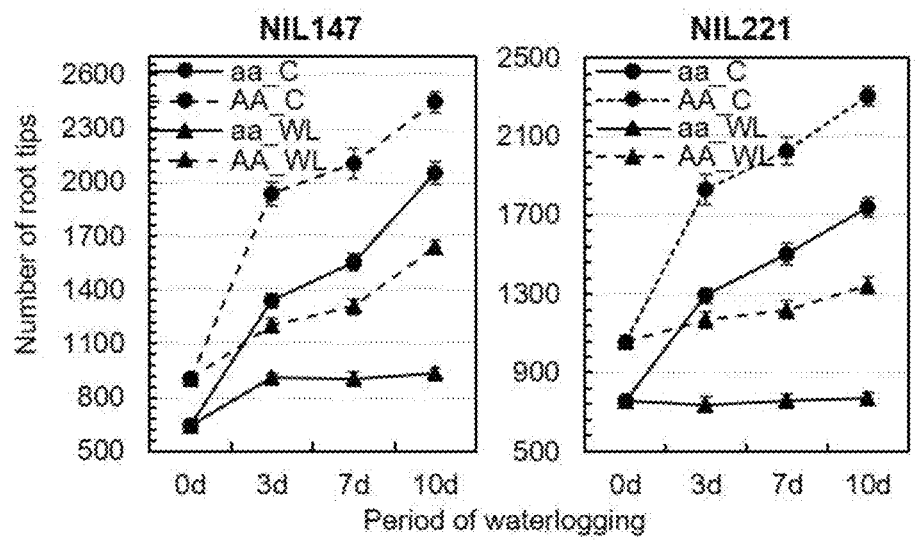
Figure 5D:
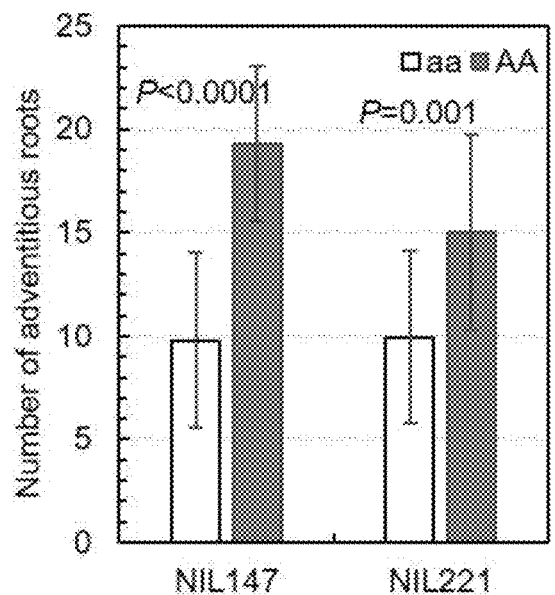
Figure 12A:
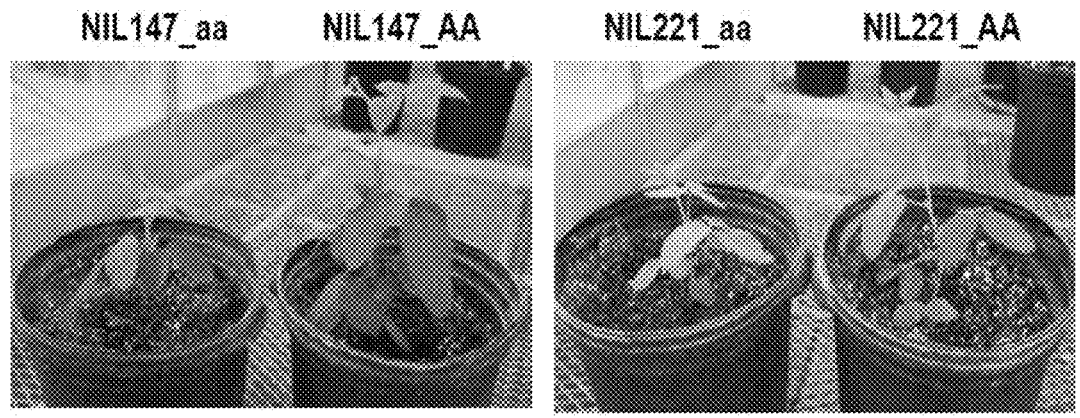
FIGS. 12A and 12B depict genotypic differences in plant recovery after transplanting.
Figure 12B:
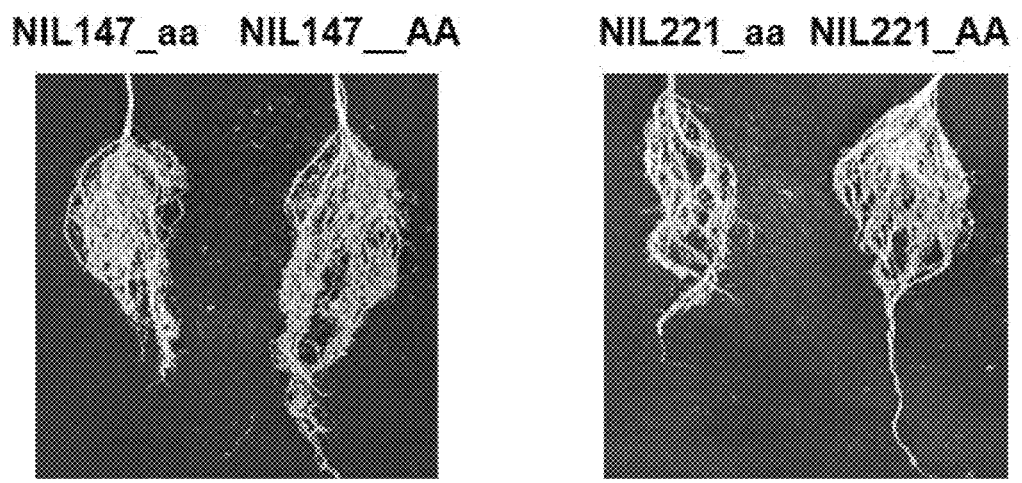

The Tolerant Allele of qWL_Gm03 Promotes Root Growth and Adventitious/Aerial Root Formation to Overcome Waterlogging Stress Initially, faster growth of shoots (FIG. 12A) and regeneration of roots (FIG. 12B) after transplanting (root damages) were observed in the tolerant NILs with tolerant allele than the sensitive NILs with the sensitive allele. It appeared that the tolerant NILs had faster root regeneration after transplanting. Therefore, the root architectures of the NILs was further examined during waterlogging stress at the early vegetative growth stage to determine the roles qWL_Gm03 in root architectures and plasticity (FIG. 5A). Waterlogging stress significantly suppressed the root growth of all the NILs (FIGS. 5B & 5C). Differences in root growth were observed between the tolerant (NIL147/221_AA) and the sensitive NILs (NIL147/221_aa). The tolerant NILs had significant longer total root length and more root tip numbers than the sensitive NILs at both control and the same time points of waterlogging treatment (FIGS. 5B & 5C). The root growth was almost completely suppressed in the sensitive NILs after 3 days of waterlogging treatment; in the contrast, the tolerant NILs maintained a certain level of root growth during 10 days of waterlogging treatment (FIGS. 5B & 5C). During the experiment, genotypic differences in formation of adventitious roots were also noted between the tolerant and sensitive NILs, as the tolerant NILs tended to form 1.5 to 2 fold of amount of adventitious/aerial roots than the sensitive NILs (FIG. 5D). The more adventitious/aerial roots in the tolerant NILs are supposed to have roles in improving $O_2$ absorption and transportation to the waterlogged root system and potential to develop into new roots after waterlogging. Compared to the sensitive allele of qWL_Gm03, the tolerant allele promoted root growth under non-stress conditions and continued to promote root growth or regeneration under waterlogging stress or root damages. Therefore, the root architectures and plasticity regulated by qWL_Gm03 should be the key determinant for the waterlogging tolerance, due to changes in the efficiency of water and nutrient uptake during and after root damages caused by waterlogging.

Confirmation of the Function of the Putative Gene in RSA and Waterlogging Tolerance Using Transgenic Hairy Roots and Composite Transgenic Plants.

Figure 6A:
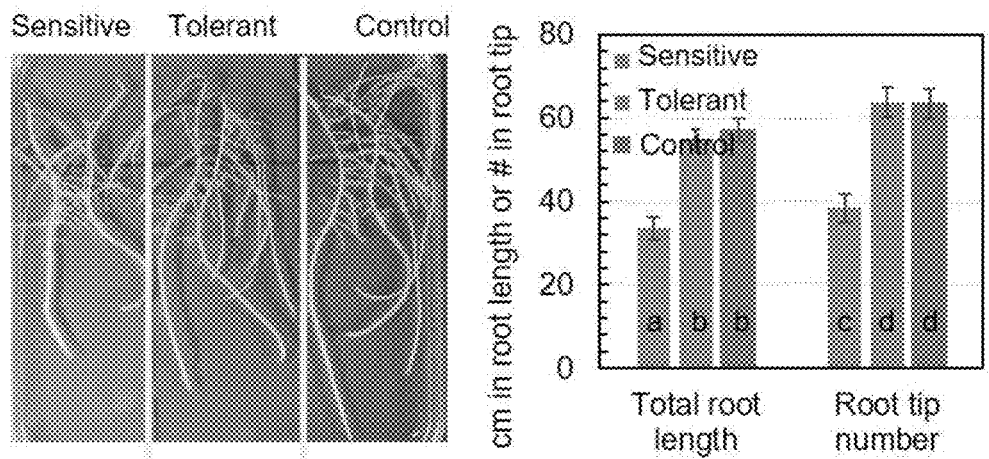
FIGS. 6A-6D depict transgenic confirmation of the effect of SAUR-FT on root growth and waterlogging tolerance.
Figure 6B:
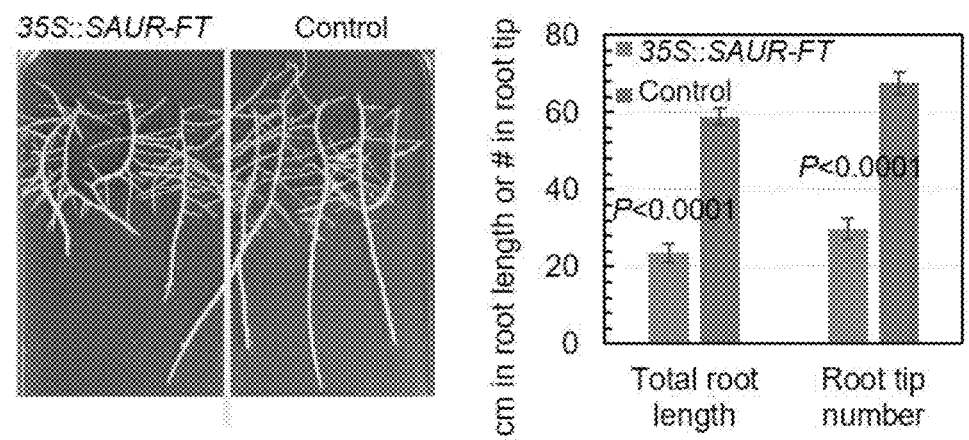
Figure 6C:
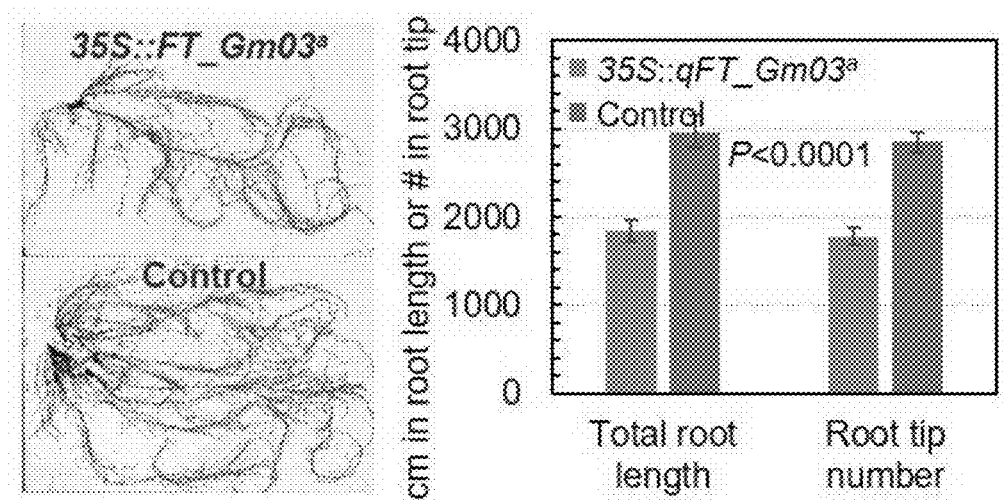
Figure 6D:
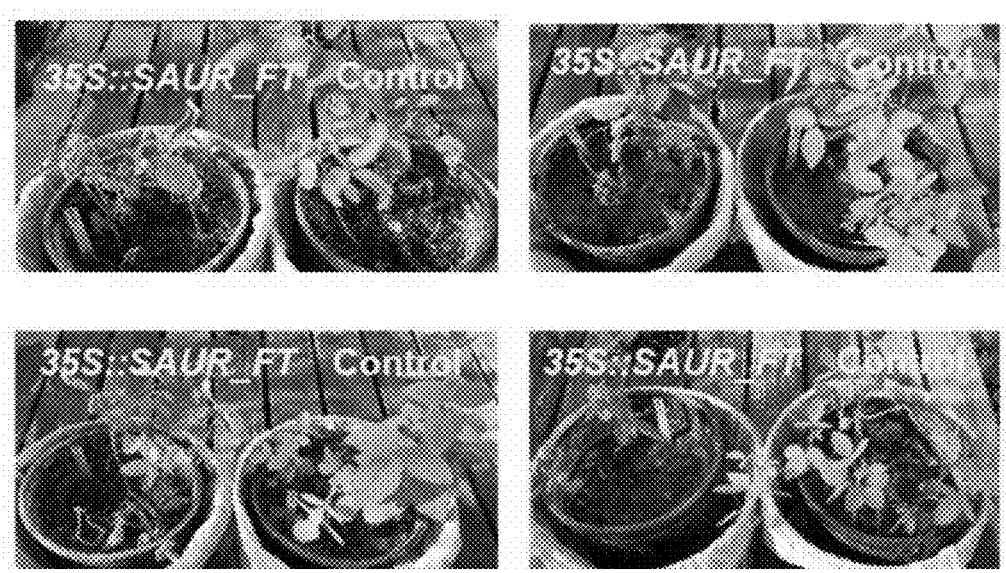

An initial study of the candidate gene in root growth was conducted using the transgenic hairy root system (FIGS. 6A-6D). Using the native promoter through the 5'UTR, protein coding region and 3'UTR, the tolerant allele of SAUR-FT did not show any significant effect on root growth compared to the empty control vector, whereas the sensitive allele decreased both total root length (39%) and root tip number (40%) compared to the control and the tolerant allele (FIG. 6A). Overexpression of the SAUR-FT (coding region only) in the hairy roots was found to be more effective than the native sensitive allele in the reduction (50% and 56%) of total root length and root tip number (FIG. 6B). The subsequent evaluation on roots and waterlogging tolerance of composite transgenic plants (transformed roots/wildtype shoot) confirmed the functions of SAUR-FT in root growth and waterlogging tolerance in soil, as overexpression of the SAUR-FT can significantly suppress root growth and reduce waterlogging tolerance (FIGS. 6C & 6D). These results indicated that allelic variation in SAUR-FT cases functional differentiation in root growth, which likely affects waterlogging tolerance; and functions of SAUR-FT in root growth and waterlogging tolerance have been confirmed.

Waterlogging Tolerance Regulated by qWL_Gm03 Involvement in Auxin Pathways

Figure 7A:
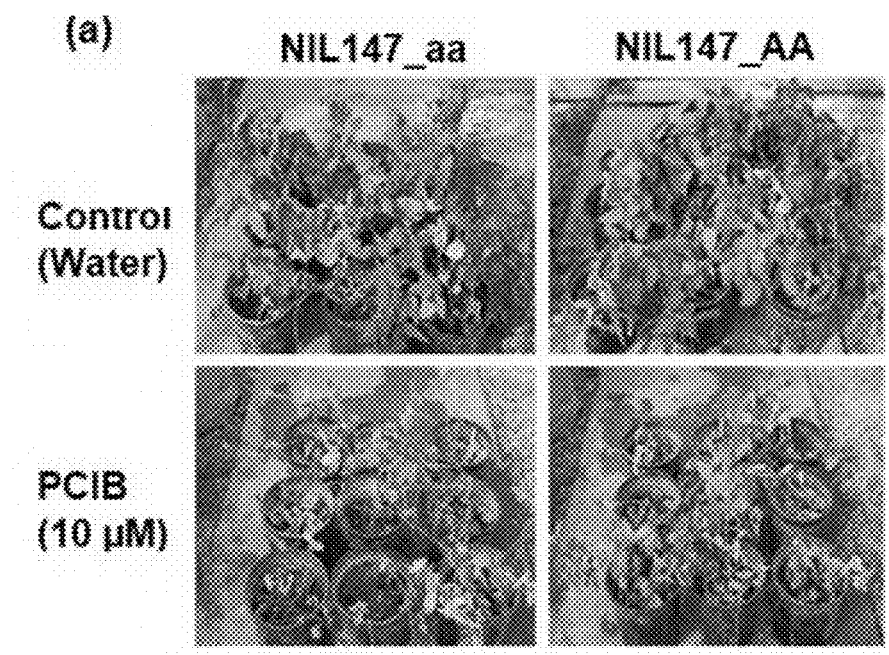
FIGS. 7A-7C depict involvement of auxin in the regulation of waterlogging tolerance. Complementation of qWL_Gm03 by auxin biosynthesis inhibitor in waterlogging tolerance (FIG. 7A) and induction of adventitious roots (FIG. 7B). The two lines were waterlogging treated for 10 days using water (control) and 10 μM p-Chlorophen-oxy-isobutyric acid (PCIB: an auxin biosynthesis inhibitor). Then plants were allowed to recover for 7 days (left) before evaluation for flooding injury scores and adventitious root rating. Data shown are means±standard deviations of 9 biological replicates (soil pots) and each replicate contains 2 to 3 plants. Student's-t-test was used to compare means between NIL147_aa and NIL147_AA.
Figure 7B:
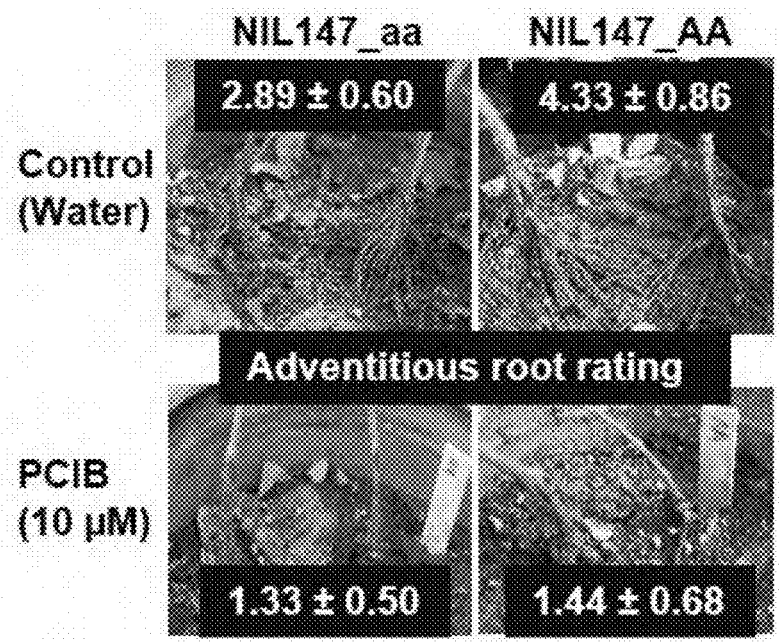
Figure 7C:
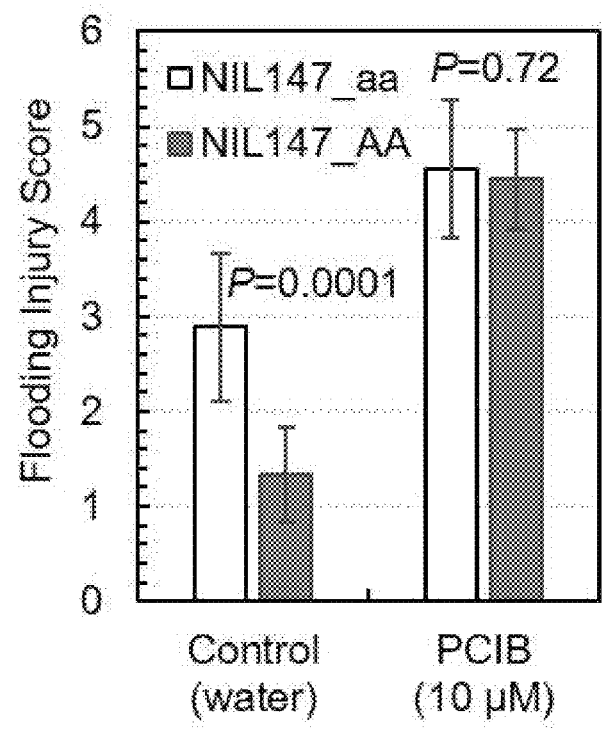
Figure 7C:
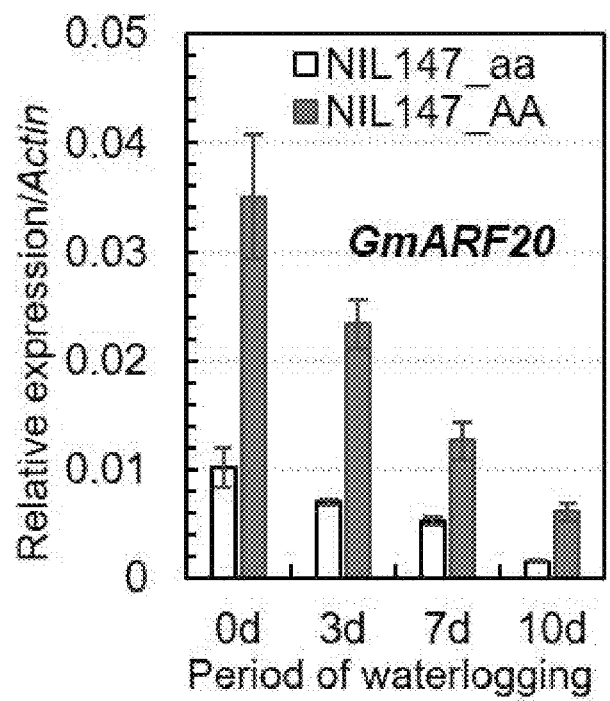

Auxin generally promotes root initiation and elongation (reviewed by Overvoorde et al. 2010). Therefore, the involvement of auxin in waterlogging tolerance was further evaluated by the treatment of an auxin biosynthesis inhibitor: p-Chlorophen-oxyisobutyric acid (PCIB) on the NILs (NIL147_aa and NIL147_AA) during waterlogging. Treatment of 10 μM PCIB was found to significantly impair waterlogging tolerance and formation of adventitious/aerial roots of the NILs (FIGS. 7A & 7B). In addition, this auxin biosynthesis inhibitor was found to complement the genotypic differences of qWL_Gm03 in waterlogging tolerance performance and formation of adventitious/aerial roots (FIGS. 7A & 7B). These results taken together indicates that the natural variant of qWL_Gm03 is likely involved in auxin pathways to regulate root growth, adventitious/aerial root formation and waterlogging tolerance. This was confirmed the inducing effect of the tolerant allele on the expression of a key factor (GmARF20: closest homologue of AtARF19) controlling secondary root development through the auxin pathways (Ha et al. 2013) between the NILs during waterlogging, compared with the sensitive allele (FIG. 7C).

Figure 8A:
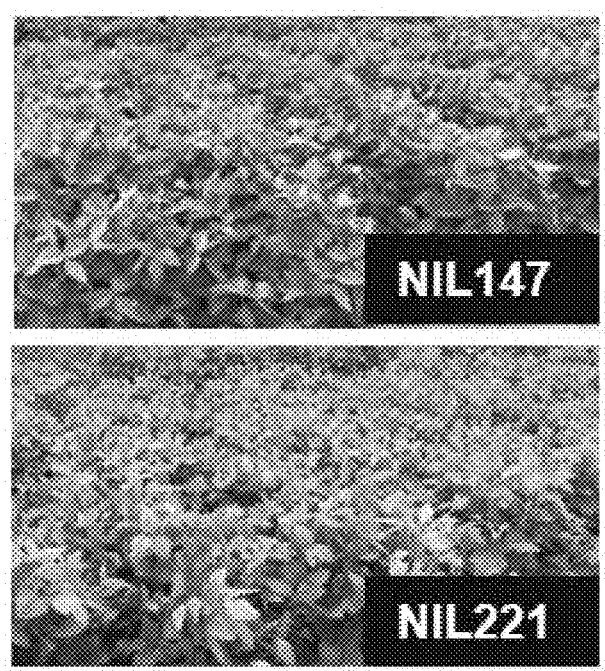
FIGS. 8A-8F depict roles of qWL_Gm03 in yield.
Figure 8B:
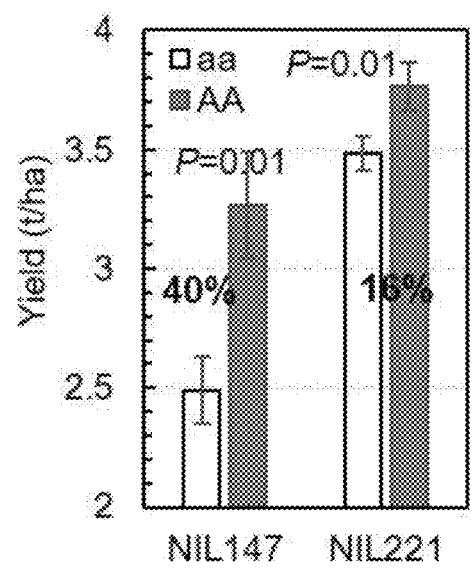
Figure 8C:
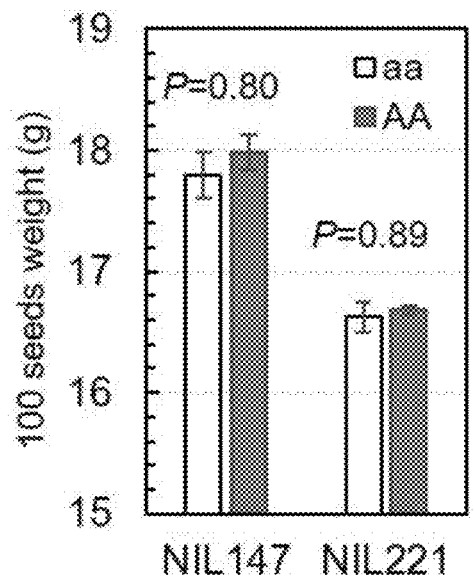
Figure 8D:
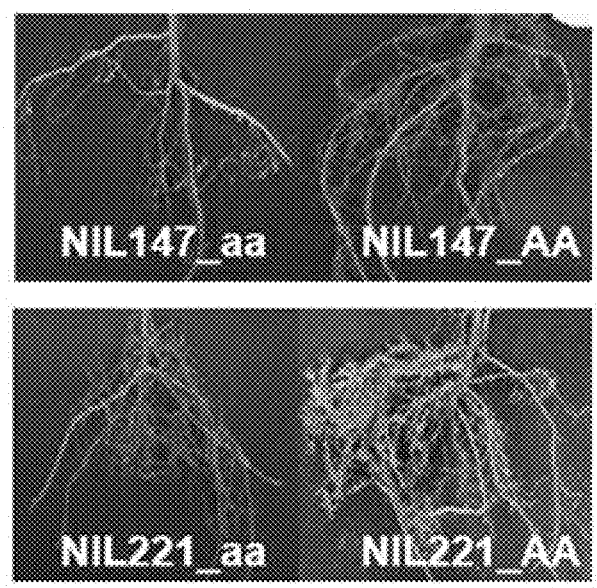
Figure 8E:
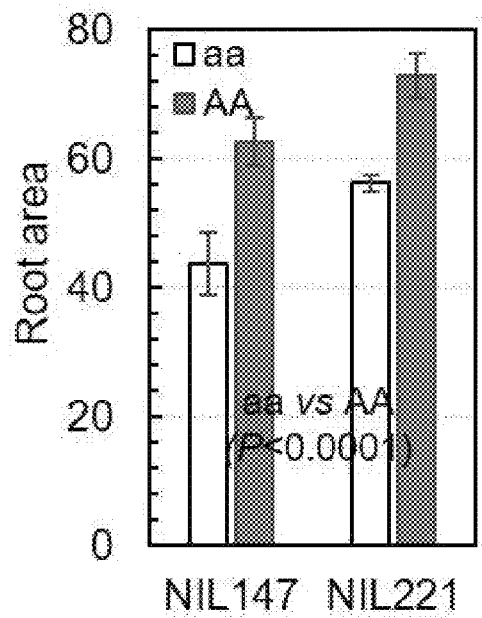
Figure 8F:
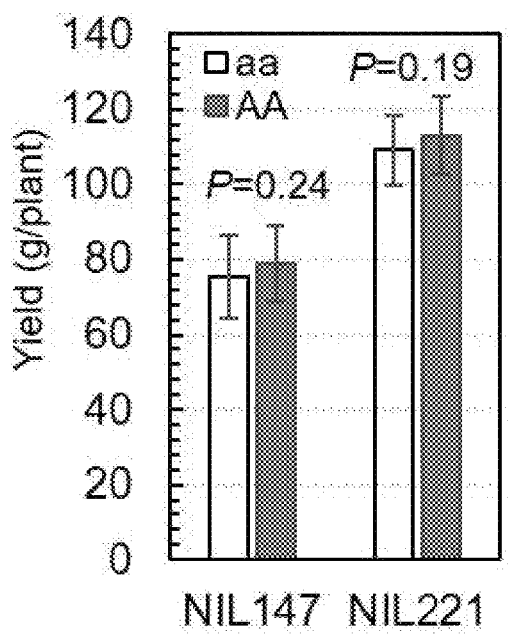

The Tolerant Allele "A" of qWL_Gm03 Improved Yield in the Field and Drought Tolerance in the Greenhouse Through Better Root System The two sets of NILs were also evaluated for the potential roles of qWL_Gm03 in the agricultural production system. The tolerant and sensitive NILs looked similar in the field (FIG. 8A). However, the tolerant NILs was found to have significantly higher yield potential than the sensitive NILs, with yield advantages of 16% to 40% (FIG. 8B). There was no significant difference in 100 seed weight (FIG. 8C), which suggested that the tolerant allele "A" of qWL_Gm03 improved yield by increasing seed numbers. The root traits were dogged out for comparison between the tolerant and sensitive NILs (FIG. 8D). The tolerant NILs had better root system than the sensitive NILs with up to 30% increase in root area (FIG. 8E). The yield per plant was further evaluated in the greenhouse. The tolerant NILs yielded a little more than the sensitive NILs, however, the differences were not significant (FIG. 8F). These results indicated that the yield advantage of tolerant allele over the sensitive allele of qWL_Gm03 was due to more efficient water and nutrient uptake, as the difference in yield between the tolerant and sensitive NILs became non-significant when sufficient water and nutrient were supplied in the greenhouse.

Figure 9A:
FIGS. 9A-9D depict roles of qWL_Gm03 in drought tolerance. (a) Images of the NILs in the greenhouse. Twenty plants for each line were planted in soil cones (1.2 m deep and 20 cm in diameter). Drought stress by withholding water was applied to plants at R1 growth stage for 14 days. (b) Water potentials of the NILs during drought stress. Data shown are means±standard deviations of 10 plants for each line at each data point. (c) Water contents of the NILs after drought treatment. Data shown are means±standard deviations of 10 plants for each line. (d) Root length densities of the NILs. Roots were harvested after the experiment. The scanned images of roots were analyzed using WinRhizo Pro software. Data shown are means±standard errors of 20 plants for each line. Student's-t-tests were performed to compare means of traits between NILs with the sensitive allele "aa" and the tolerant allele "AA".
Figure 9B:
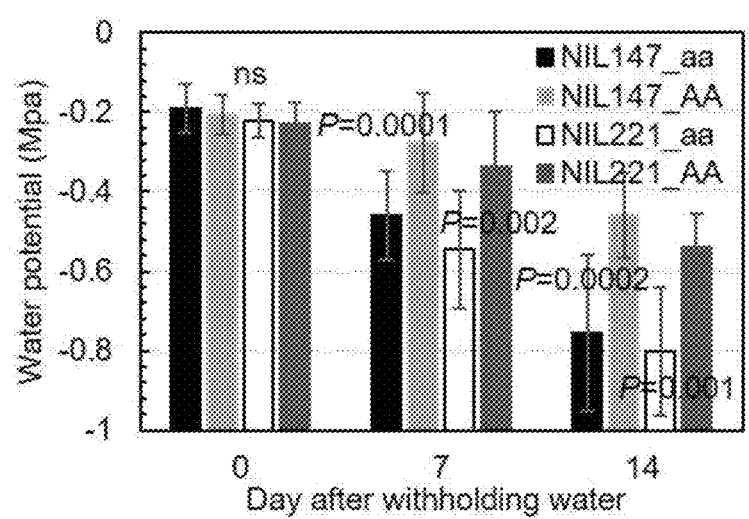
Figure 9C:
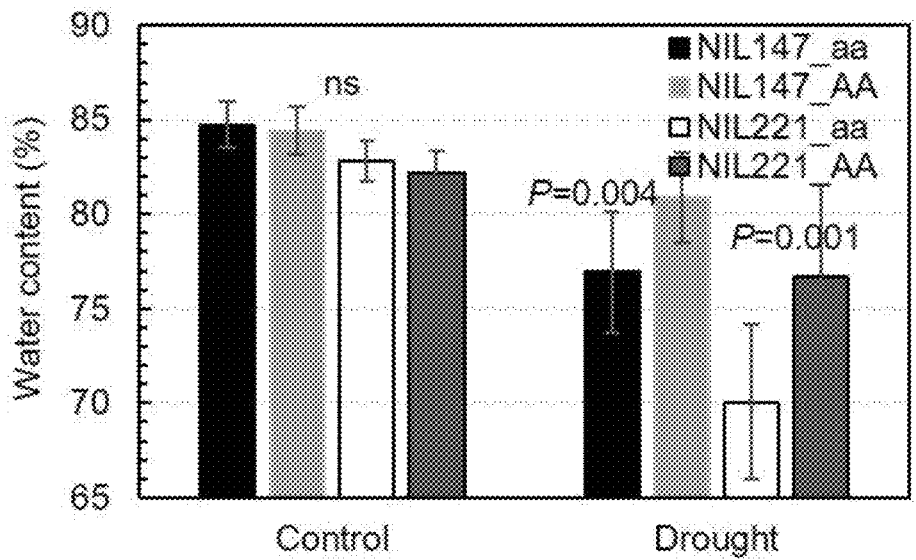
Figure 9D:
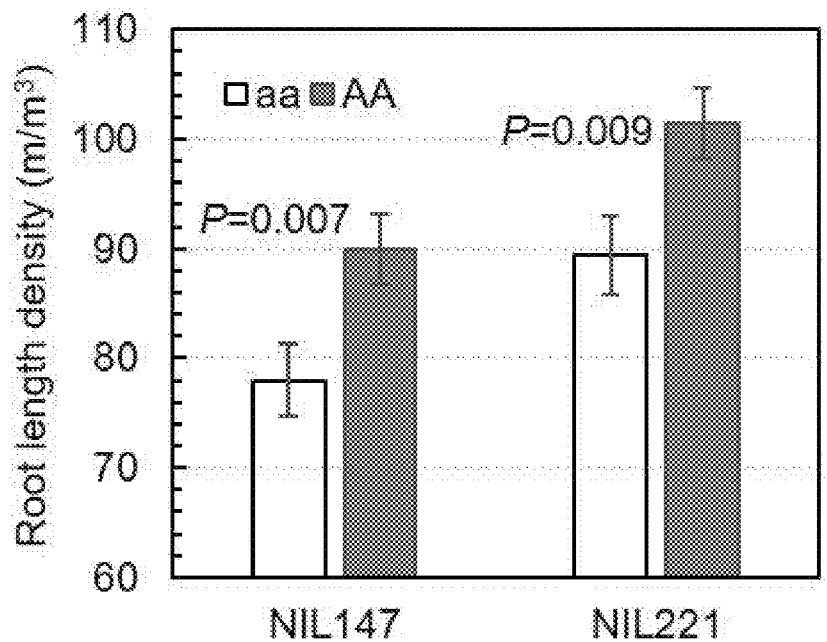

Better root system is generally thought to help water uptake under water limited (drought) conditions. Therefore, the roles of the better roots regulated by qWL_Gm03 in drought tolerance were further evaluated in soil cones (1.2 m deep and 20 cm in diameter) under the greenhouse conditions at R1 growth stage (FIG. 9A). Under control conditions (well-watered), there was no difference in water potentials and water contents of plants between the tolerant and sensitive NILs; however, during drought treatment, the tolerant NILs were identified to maintain better water status than sensitive NILs (FIGS. 9B & 9C). The tolerant NILs developed higher root length densities than the sensitive NILs with an increase up to 15% (FIG. 9D). These results provided direct evidence to emphasize the importance of roots in crop improvement and indicated that the natural variant of qWL_Gm03 could benefit plants under nonstress conditions and other abiotic stress, such as drought.

Two novel waterlogging tolerance loci were identified in the RIL population in this study and they were affected largely by environment. The effects and contributions of the two QTL varied across years and the minor one was even undetectable in 2015. However, the major one qWL_Gm03 is fairly stable with relatively largest effect ($R^2$ up to 33%) among all previously reported waterlogging QTL (VanToai et al. 2001; Cornelious et al. 2005 & 2006; Nguyen et al. 2012). Isolation of the major QTL at the NIL backgrounds successfully confirmed this QTL with increased phenotypic contributions (up to 47.4%) due to more synchronized genetic backgrounds. At the NIL backgrounds, qWL_Gm03 continued to show quantitative characteristics, as the same genotypes showed continuous phenotypic distributions (FIGS. 3A & 3B) and its phenotypic contributions varied among populations and years (FIGS. 3A, 2B & 4). Waterlogging tolerance evaluation of the NILs also confirmed the effectiveness of qWL_Gm03 in improving soybean waterlogging tolerance at different environments (FIG. 3D). In addition, the tolerant allele of qWL_Gm03 can improve yield under non-stress field conditions (FIG. 8B) and drought tolerance under the greenhouse conditions (FIGS. 9B & 9C). These agronomic benefits of the tolerant allele of qWL_Gm03 should be accounted by its ability to develop better root system (FIGS. 8E & 9D). When sufficient water and nutrient were supplied as under the greenhouse conditions, the yield advantage of the tolerant allele was not significant (FIG. 8F). However, these optimum conditions were unable to be achieved in the agricultural production systems. Therefore, it is valuable to introduce the tolerant allele of qWL_Gm03 into the current elite germplasm from exotic resources, which could result in not only the tolerance to the major abiotic stresses, but also the overall yield improvement in the field.

The initial fine-mapping with progeny tests narrowed qWL_Gm03 into a genomic region of <380-Kbp containing 30 predicted genes based on Williams 82 reference genome (FIG. 4) (Schmutz et al. 2010; Grant et al. 2010). Currently, the identified polymorphic SNP markers (FIG. 4) in the candidate region of qWL_Gm03 can be used in marker-assisted selection for the tolerant allele at qWL_Gm03 in soybean breeding.

Roots have been recognized as one of the most important parts for crop improvement for yield and drought tolerance (Kramer 1969). Benefit of a better root system on crop improvement has been reported in various crops (Nguyen et al. 1997; Forster et al. 2005; Hund et al. 2011; Sadok & Sinclair 2011; Wasson et al. 2012; Uga et al. 2013). The first natural variation cloned for deeper and more proliferous rooting was cloned as Dro1 in rice, which could improve yield under both non-stress and drought conditions (Uga et al. 2013; Arai-Sanoh et al. 2014). In this example, another natural variation involved in root growth was reported to improve yield and tolerance to abiotic stresses.

Figure 10:
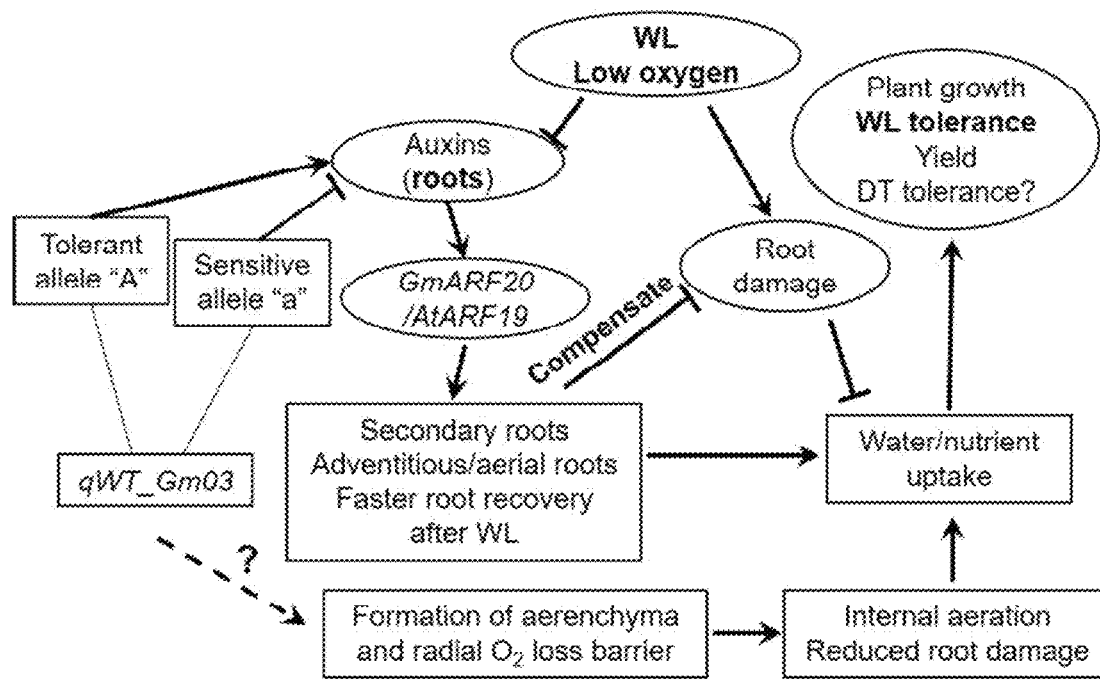
FIG. 10 depicts a hypothesized model of waterlogging tolerance regulated by qWL_Gm03. Arrows indicate enhancement or promotion and bars indicate inhibition or suppression. The arrows or bars suggest the enhancing or impairing effects, respectively. "WL" and "DT" stand for waterlogging and drought, respectively.

Roots directly face damage during waterlogging stress due to cellular anoxia, with root meristems showing particular vulnerability (Kozlowski 1984; Valliyodan et al. 2014). Damaged root system fails in water and nutrient uptake, especially after waterlogging relieved (soil drying). (Kramer & Jackson 1954). Moreover, soybean plants usually show flooding injury several days after removal of waterlogging stress as the soil dries possibly due inability to uptake enough water to support above-ground tissues (Nguyen et al. 2012). Previously, several waterlogging tolerant soybean lines were found to have favorable root growth under waterlogging stress (Sakazono et al. 2014; Jitsuyama 2015; Kim et al. 2015); however, this knowledge does not allow for making conclusions as whether the favorable root growth under waterlogging stress is the determinant or consequence of waterlogging tolerance. It is possible that the favorable root growth is just the outlooks of waterlogging tolerance as the lighter waterlogging injury of the shoots. In this example, NILs with the tolerant allele showed more favorable root growth under nonstress condition and continued to show more favorable root plasticity under stress and root damages, to facilitate adequate water and nutrient uptakes in the stress or recovery phases to support the above-ground tissues to overcome the stress (FIGS. 5 & 12). Therefore, direct evidence to support determinant roles of root architectures and plasticity in the regulation of waterlogging tolerance was obtained under the NIL genetic background. The abiotic stress tolerance mechanisms usually require plants to suspend growth of unnecessary tissues to reserve energy and resources during stress periods, but to promote growth of necessary tissues to avoid stresses, especially for flooding caused abiotic stresses, for example as submergence tolerance (Reviewed by Bailey-Serres et al. 2012; Fukao & Xiong 2013; Voesenek & Bailey-Serres 2015). Similar strategy in waterlogging tolerance was revealed for dryland crop. The natural variant of qWL_Gm03 maintained (instead of inhibited) secondary root growth and adventurous/aerial root formation to compensate root damages due to waterlogging, which can avoid the insufficient water and nutrient uptake caused by waterlogged roots (FIG. 10).

Auxin promotes plant growth by stimulating cell division, elongation and differentiation (reviewed by Teale et al. 2006). Auxin plays roles in secondary root initiation and elongation (reviewed by Overvoorde et al. 2010). In this example, the involvement of auxin pathways in the regulation of waterlogging tolerance were found (FIGS. 7A & 7B) and the expression of one of the auxin-downstream genes (GmARF20) was altered between the NILs under both non-stress and waterlogging conditions (FIG. 7C). Therefore, qWL_Gm03 may be involved in the auxin pathways to induce one of the key factors (GmARF20) for secondary root development and exhibition of more favorable root plasticity (FIG. 10).

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A modified soybean plant comprising at least one of a modified 5'-untranslated region of a Glyma.03g029600 gene, wherein the modified 5'-untranslated region comprises an insertion in a 5'-untranslated region at a site located from 1 base pair nucleotide to 780 base pair nucleotides from the transcription initiation start site wherein the modified soybean plant comprises a trait of increased waterlogging tolerance as compared to a soybean plant not having the modified 5'-untranslated region of the Glyma.03g029600 gene.

2. The modified soybean plant of claim 1, wherein the insertion comprises a poly-A insertion.

3. The modified soybean plant of claim 2, wherein the poly-A insertion is an 11 base pair insertion.

4. The modified soybean plant of claim 1, comprising about 1.5-fold to about 2-fold more adventitious/aerial roots than a soybean plant not comprising the modified 5'-untranslated region of Glyma.03g029600 gene.

5. The modified soybean plant of claim 1, wherein the soybean plant comprises at least one of an increased total root length and an increased root tip number as compared to a soybean plant not having the modified 5'-untranslated region of Glyma.03g029600 gene.

6. A soybean seed, a soybean plant cell, or a progeny of the soybean plant according to claim 1, wherein the soybean seed, soybean plant cell or progeny of the soybean plant comprises a Glyma.03g029600 gene with a modified 5'-untranslated region wherein the mutation comprises an insertion in the 5' UTR at a site located from 1 base pair nucleotide to 780 base pair nucleotides from the transcription initiation start site.

7. A method of selecting a soybean plant having increased waterlogging tolerance, the method comprising obtaining a sample of the soybean plant and detecting an insertion in a 5'-untranslated region at a site located from 1 base pair nucleotide to 780 base pair nucleotides from the transcription initiation start site in the Glyma.03g029600 gene.

8. The method of claim 7, wherein the soybean plant is determined to have increased waterlogging tolerance when the Glyma.03g029600 gene 5'-untranslated region comprises a poly-A insertion.

9. The method of claim 8, wherein the poly-A insertion comprises at least an eleven (11) base pair poly-A insertion.

10. A method of producing a modified soybean plant having increased waterlogging tolerance, the method comprising: reducing expression of Glyma.03g029600 by creating an insertion in a 5'-untranslated region of the Glyma.03g029600 gene at a site located from 1 base pair nucleotide to 780 base pair nucleotides from the transcription initiation start site.

11. The method of claim 10, wherein the insertion comprises a poly-A insertion.

12. The method of claim 11, wherein the poly-A insertion comprises at least an eleven (11) base pair insertion.

* * * * *